(12) United States Patent
Tachibana et al.

(10) Patent No.: US 6,342,239 B1
(45) Date of Patent: Jan. 29, 2002

(54) POWDER COMPOSITION, A POWDER DISPERSION IN OIL AND A COSMETIC COMPOSITION CONTAINING SAID POWDER COMPOSITION AND A POWDER DISPERSION IN OIL

(75) Inventors: Kiyomi Tachibana; Toru Shimizu, both of Kita-ku (JP)

(73) Assignee: KoséCorporation, Tokyo (JP)

( * ) Notice: Subject to any disclaimer, the term of this patent is extended or adjusted under 35 U.S.C. 154(b) by 0 days.

(21) Appl. No.: 09/679,072

(22) Filed: Oct. 5, 2000

Related U.S. Application Data

(63) Continuation of application No. 09/226,150, filed on Jan. 7, 1999, now abandoned.

(30) Foreign Application Priority Data

Jan. 13, 1998 (JP) .............................................. 10-18217
Jan. 13, 1998 (JP) .............................................. 10-18218

(51) Int. Cl.$^7$ ......................... A61K 7/06; A61K 7/035; A61K 7/48; A61K 7/027; A61K 9/14
(52) U.S. Cl. ................. 424/401; 424/78.03; 424/70.12; 424/70.122; 424/60; 424/69; 424/64; 514/844; 514/846
(58) Field of Search ................................ 424/489, 490, 424/64, 69, 70.1, 70.7, 70.12, 70.122, 59, 60, 78.03; 514/844, 846

(56) References Cited

FOREIGN PATENT DOCUMENTS

| JP | 05339125 | 12/1993 |
|---|---|---|
| JP | 05339518 | 12/1993 |
| JP | 06009332 | 1/1994 |

*Primary Examiner*—James M. Spear

(57) ABSTRACT

A powder composition comprising, a copolymer containing (A) an organopolysiloxane monomer, one or more kinds of monomer selected from a group composed by (B) a monomer containing nitrogen group, a monomer possessing a polyoxyalkylene group, a monomer possessing a polylactone group, a monomer possessing a hydroxyl group and a monomer possessing an anionic group and a powder. Further, a powder dispersion in oil comprising said copolymer, powder and oil, and a cosmetic composition containing them. Said powder composition and a powder dispersion in oil have a less cohesion of powder particles and is superior in a dispersing ability and a dispersion stability, and the cosmetic composition which contains said powder composition has a good stability and gives an excellent sensation at the actual use.

31 Claims, No Drawings

POWDER COMPOSITION, A POWDER DISPERSION IN OIL AND A COSMETIC COMPOSITION CONTAINING SAID POWDER COMPOSITION AND A POWDER DISPERSION IN OIL

This application is a continuation of Ser. No. 09/226,150 filed Jan. 7, 1999, now abandoned.

DETAILED DESCRIPTION OF THE INVENTION

1. Background of the Invention

This invention relates to a powder composition having good dispersing ability treated by a copolymer containing (A) an organopolysiloxane monomer and (B) one or more kinds of monomer selected from a group composed by a monomer containing nitrogen group, a monomer possessing a polyoxyalkylene group, a monomer possessing a polylactone group, a monomer possessing a hydroxyl group and a monomer possessing an anionic group, and a powder dispersion in oil comprising a said copolymers, powder and oil, further relates to a cosmetic composition containing a said powder composition and powder dispersion in oil.

2. Description of the Prior Art

Occasionally, powder which is not treated has problems such as cohesion based on electric charge or polar which powder surface has or deterioration of affinity to solvent based on interfacial tension of powder. To solve these problems and to improve dispersing ability, dispersion stability and feeling at actual use, various methods for surface treatment of powder by various kinds of improving agent are proposed.

Treating agents and methods which are used for the surface treatment are different according to each purpose, and are selected considering the surface property or the affinity to solvents. For example, lipophilic treatment by oil or metallic soap, hydrophilic treatment by surface active agent or aqueous polymer, water repellent or oil repellent treatment by silicone oil or others are well known.

OBJECT OF THE INVENTION

However, although these surface treated powder are improved by above mentioned methods, effects to avoid cohesion and sedimentation are not sufficient. And when the treating agent or treating method is not suited, various troubles occur, for example, powder and treating agent are dissociated in a cosmetic composition and the powder coheres and sediments by aging, or re-dispersing ability is deteriorated and the quality of products and the feeling at use are spoiled.

The object of the present invention is to provide a powder composition and a powder dispersion in oil which have less cohesiveness and is superior at dispersing ability, further a cosmetic composition which has an excellent sensation upon use and a good stability by containing a said powder composition and powder dispersion in oil.

BRIEF SUMMARY OF THE INVENTION

The inventors of this invention have conduced earnest study and found that the above mentioned problems can be solved by using a copolymer which has a specific construction and feature, and accomplished the present invention.

That is, the present invention is, a powder composition comprising a copolymer containing (A) an organopolysiloxane monomer, and one or more kinds of monomer selected from a group composed by (B) a monomer containing nitrogen group, a monomer possessing a polyoxyalkylene group, a monomer possessing a polylactone containing group, a monomer possessing a hydroxyl group and a monomer possessing an anionic group, and a powder dispersion in oil composed by a said copolymers, powder and oil, further relates to a cosmetic composition containing a said powder composition and powder dispersion in oil.

DISCLOSURE OF THE INVENTION

A copolymer which can be used in this invention is the copolymer which contains (A) an organopolysiloxane monomer and (B) a monomer containing nitrogen group or a monomer possessing a polyoxyalkylene group, a monomer possessing a polylactone containing group, a monomer possessing a hydroxyl group and a monomer possessing an anionic group as the construction component.

As an organopolysiloxane monomer of (A), it is desirable to be an organopolysiloxane monomer having radical polymerization group which can copolymerize with (B) monomer, concretely vinyl group, and organopolysiloxane monomer represented by following general formula (I) can be mentioned.

$$W(X)_a Si(Y)_b (Z)_c \qquad (1)$$

In this formula, W represents a vinyl group, X represents a divalent bonding group, Y represents a hydrogen atom, an alkyl group of carbon number 1~10, an aryl group or an alkoxy group and Z represents a monovalent siloxane polymer, further, a is an integer of 0 or 1, b is an integer of 0~2, and c is an integer of 1~3, wherein said vinyl group can possess a substitution group and b+c=3.

Among the monomer (A), as the concrete example which can be preferably used, compounds represented by following chemical formula can be mentioned.

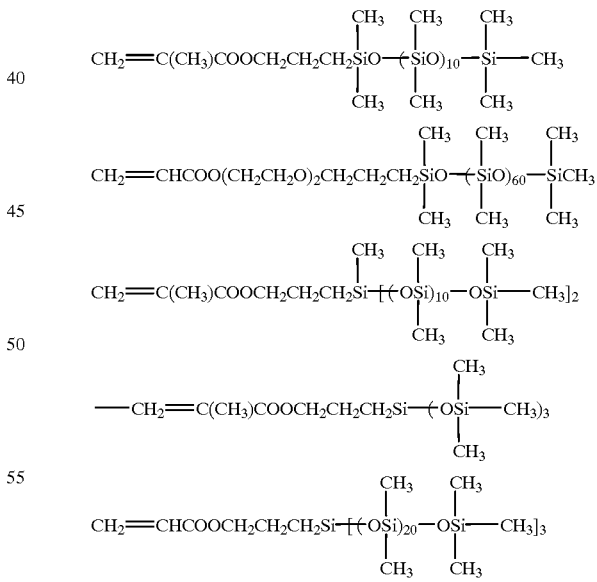

As the (B) monomer containing nitrogen group, a nitrogen containing group possessing radical polymerization group such as vinyl monomer which has nitrogen containing group can be mentioned. for example, N,N-dimethylaminoethylacrylate, N,N-diethylaminoethyl acrylate, N,N-dimethylaminoethylmethacrylate, N,N-diethyl aminoethylmethacrylate and a quaternary salt of them; acrylamide, N-methylacrylamide, N-ethylacrylamide, N-n-propylacrylamide, N-isopropylacrylamide, N-n-butyl acrylamide, N-isobutylacrylamide, N-t-butylacrylamide, N-octylacrylamide, N-octadecylacrylamide, N-phenylacrylamide, N-methylolacrylamide, N-allylacrylamide, N-diacetoneacrylamide; methacrylamide, N-methylmethacrylamide, N-ethyl methacrylamide, N-n-propylmethacrylamide, N-iso propylmethacrylamide, N-n-butylmethacrylamide, N-iso butylmethacrylamide, N-t-butylmethacrylamide, N-octyl methacrylamide, N-octadecylmethacrylamide, N-dodecylmethacrylamide, N-phenylmethacrylamide, N-methylolmethacrylamide, N-allylmethacrylamide; α-ethylacrylamide; N,N-dimethylacrylamide, N,N-diethylacrylamide, N,N-diisopropylacrylamide, N,N-di-n-butylacrylamide, N,N-dimethylmethacrylamide, N,N-diethylmethacrylamide, N,N-diisopropylmethacrylamide, N,N-di-n-butylmethacrylamide; N,N-dimethylaminoethylacrylamide, N,N-dimethylaminoethylmethacrylamide, N,N-dimethylaminopropylacrylamide, N,N-dimethylaminopropylmethacrylamide and a quaternary salt of them, N-vinyl-N,N-dimethylamine, N-vinyl-N-ethyl-N-butylamine and a quaternary salt of them; o-aminostyrene, m-aminostyrene, p-aminostyrene, o-N,N-dimethylaminostyrene, m-N,N-dimethylaminostyrene, p-N,N-dimethylaminostyrene; N-vinylpyrrolidone, N-vinyl-3-methylpyrrolidone, N-vinyl-5-methylpyrrolidone, N-vinyl-3,3,5-trimethylpyrrolidone, N-vinylpiperidone, N-vinylcaprolactam, N-vinylcaprylolactam, N-vinylformamide, N-vinylacetoamide, N-vinylpropionic acid amide, N-vinylbenzoic acid amide, N-methyl-N-vinylbenzoic acid amide, N-phenyl-N-vinylacetoamide; N-phenyl-N-vinylbenzoic acid amide, diallyldimethylammoniumchloride, N-vinylmaleicimide, vinylpyridine, N-vinylimidazole, N-vinylcarbazole, N-acylalkyleneimine whose end group is sealed and N-alkylenecarbobetaine can be mentioned, and one or more kinds selected from these compounds can be used. Especially, acrylamide, methacrylamide, N-vinylpyrrolidone and N-vinylacetoamide are preferably used.

As the (B) monomer containing polyoxyalkylene group, a monomer possessing radical polymerization group and polyoxyalkylene group, concretely a monomer possessing vinyl group and polyoxyalkylene group can be mentioned. For example a monomer possesses polyoxyalkylene group represented by following general formula (2) can be mentioned.

$$J(K)_p(Q)_sT \tag{2}$$

In the formula, J represents a vinyl group (can possess substitution group), K represents a divalent bonding group, Q represents a polyoxyalkylene group represented by —(CH$_2$)$_t$O— and T represents a hydrogen atom, an alkyl group of carbon number 1~10 or an organic group represented by R'—(CO)—, further, $_p$ is an integer of 0 or 1, $_s$ is an integer bigger than 1, $_t$ is an integer of 1~50 and R' represents alkyl group of carbon number 1~5.

Concretely, compounds represented by following chemical formula can be mentioned. These compounds can be used alone or can be used together with. Among these compounds, a monomer containing polyoxyalkylene group whose $_t$ is an integer bigger than 3 is desirably used, especially a monomer contains $_t$=3 polyoxypropylene group is more desirable.

CH$_2$=C(CH$_3$)COO(C$_2$H$_4$O)$_2$H

CH$_2$=C(CH$_3$)COO(C$_2$H$_4$O)$_4$CH$_3$

CH$_2$=CHCOO(C$_2$H$_4$O)$_7$H

CH$_2$=C(CH$_3$)COO(C$_3$H$_6$O)$_{12}$H

CH$_2$=CHCOO(C$_3$H$_6$O)$_6$H

CH$_2$=CHCOO(C$_2$H$_4$O)$_7$(C$_3$H$_6$O)$_3$H

CH$_2$=CHCOO(C$_2$H$_4$O)$_{10}$(C$_4$H$_8$O)$_5$H

CH$_2$=CHCOO(C$_2$H$_4$O)$_{16}$(C$_4$H$_8$O)$_6$H

As the (B) monomer containing polylactone group, a monomer possessing radical polymerization group and polylactone group, concretely a monomer possessing vinyl group and polylactone group can be mentioned. For example a monomer possesses polylactone group represented by following general formula (3) can be mentioned.

$$J(K)_p(L)_qM \tag{3}$$

In the formula, J represents a vinyl group (can possess substitution group), K represents a divalent bonding group, L represents a lactone group represented by —C(=O)(CR$_2$)$_r$CHRO— and M represents a hydrogen atom or an acetyl group. $_p$ is an integer of 0 or 1, $_q$ is an integer bigger than 1, $_r$ is an integer of 4~6 and R represents a hydrogen atom or an alkyl group of carbon number 1~12.

For example, said compound can be obtained by ring-opening reaction of δ-valerolactone, ethyl-δ-valerolactone, ε-caprolactone, methyl-ε-caprolactone, ethyl-ε-caprolactone, dimethyl-ε-caprolactone, trimethyl-ε-caprolactone and enanthonolactone.

Concretely, compounds represented by following general formulae can be mentioned. Especially, ε-caprolactone are desirably used.

—CH$_2$=C(CH$_3$)COOCH$_2$CH$_2$O(C(=O)C$_5$H$_{10}$O)$_3$H

CH$_2$=CHCOO(CH$_2$CH$_2$O)$_2$CH$_2$CH$_2$O(C(=O)C$_5$H$_{10}$O)$_3$H

CH$_2$=C(CH$_3$)COOCH$_2$CH$_2$O(C(=O)C$_5$H$_{10}$O)$_3$C(=O)CH$_3$—.

As a monomer of the (B) monomer possessing hydroxyl group, a monomer possessing a radical polymerization group and hydroxyl group, concretely a monomer possessing a vinyl group and a hydroxyl group represented by general formula (4) is desirably used.

$$J(K)_sU \tag{4}$$

In the formula, J represents a vinyl group (can possess substitution group), K represents a divalent bonding group and U represents organic group possessing a hydroxide group, further, $_s$ represents integer number of 0 or 1.

Concretely, the compounds represented by following chemical formulae can be mentioned. These compounds can be used alone or can be used together with.

CH$_2$=CHCOOCH$_2$CH$_2$OH

CH$_2$=CHCOOCH$_2$CH(OH)CH$_3$

CH$_2$=C(CH$_3$)COOCH$_2$CH$_2$OH

CH$_2$=C(CH$_3$)COOCH$_2$CH(OH)CH$_3$

CH$_2$=C(CH$_3$)COOCH$_2$CH(OH)CH$_2$OH

CH$_2$=CHCOOCH$_2$CH$_2$OCO(C$_6$H$_4$)COOCH$_2$CH(OH)CH$_3$ $CH_2=CHCOOCH_2CH(OH)CH_2OC_6H_5$ $CH_2=CHCOOCH_2CH_2CH_2CH_2OH$

As the (B) monomer containing an anionic group, a monomer possessing a radical polymerization group and an anionic group, concretely a monomer possessing a vinyl group and an anionic group can be mentioned, and as the anionic group, a carboxylic acid group, a phosphoric acid group and a sulfonic acid group can be mentioned.

Concretely, acrylic acid, methacrylic acid, maleic acid, maleic anhydride, itaconic acid, fumaric acid, crotonic acid, monomer containing a carboxyl group such as half ester between polybasic anhydride acrylic acid and methacrylic acid containing hydroxyl group, monomer containing a phosphate group such as mono(2-hydroxyethyl) methacrylicphosphate, and monomer containing sulfonate group such as styrenesulfonic acid, sulfoethylacrylate, sulfoethylmethacrylate can be mentioned. Neutralized type of them can be also used. These compounds can be used alone or can be used together with.

Further, in the copolymer of this invention, when above mentioned (A) monomer and (B) monomer is a monomer which possesses a radical polymerization group, it can be possible to copolymerize with other compound which can copolymerize with them. As the example of said compound alkyl methacrylate such as methyl methacrylate, ethyl methacrylate, n-butyl methacrylate, 2-ethylhexyl methacrylate, stearyl methacrylate, behenyl methacrylate; perfluoroalkyl(metha)acrylate of fluoro carbon chain 1~10, styrene, substituted styrene, vinyl acetate, maleic acid diester, fumaric acid diester, vinyl chloride, vinylidene chloride, ethylene, propylene, buthadiene, acrylonitrile and olefin fluoride can be mentioned.

As the powder used in this invention, any kinds of powder which are used in the conventional cosmetic composition can be used without adhere to the shape (spherical, needle-shape, plate-shape), particle size (mist like, fine particle, pigment size) or structural feature of particle (high porosity, no pore).

For example, as the inorganic powder, titanium oxide, zirconium oxide, zinc oxide, cerium oxide, magnesium oxide, barium sulfate, calcium sulfate, magnesium sulfate, calcium carbonate, magnesium carbonate, talc, mica, kaolin, sericite, muscovite, synthetic mica, phlogopite, lepidolite, biotite, lithia mica, silicic acid, silicic acid anhydride, aluminium silicate, magnesium silicate, aluminium magnesium silicate, calcium silicate, barium silicate, strontium silicate, metallic salt of tungstic acid, hydroxy apatite, vermiculite, bentonite, montmorillonite, hectorite, zeolite, ceramics powder, calcium secondary phosphate, alumina, aluminium hydroxide, boron nitride and silica can be mentioned.

As the organic powder, polyamide powder, polyester powder, polyethylene powder, polypropylene powder, polystyrene powder, polyurethane powder, benzoguanamine powder, polymethyl benzoguanamine powder, tetrafluoroethylene powder, polymethylmethacrylate powder, cellulose powder, silk powder, nylon powder, 12-nylon, 6-nylon, styrene.acrylic acid copolymer, divinylbenzene.styrene copolymer, vinyl resin, urea resin, phenol resin, fluorine-contained resin, silicone resin, acrylic resin, melamine resin, epoxy resin, polycarbonate resin, fine crystalline fiber powder, rice starch, corn starch, lauroyl lysine; as the metallic soap powder, zinc stearate, aluminium stearate, calcium stearate, magnesium stearate, zinc myristate, magnesium myristate, zinc cetyl phosphate, calcium cetyl phosphate, zinc sodium cetyl phosphate; as the colored pigment, inorganic red pigment such as iron oxide, iron hydroxide and iron titanate, inorganic brown color pigment such as γ-iron oxide, inorganic yellow color pigment such as yellow iron oxide and loess, inorganic black pigment such as black iron oxide and carbon black, inorganic violet pigment such as manganese violet and cobalt violet, inorganic green pigment such as chromium hydroxide, chromium oxide, cobalt oxide and cobalt titanate, inorganic blue pigment such as prussian blue and ultramarine, lake formed tar pigment, lake formed natural coloring matter and mixed powder of these powder.

As the pearl pigment, titanium oxide coated mica, bismuth oxychrolide, titanium oxide coated bismuth oxychrolide, titanium oxide coated talk, fish scale flake and titanium oxide coated colored mica as the metal powder pigment, aluminium powder, copper powder, stainless steel powder; as the tar pigment, Erythrosine (Acid Red, C.I.45430, FD&C Red No.3), Phloxyne B (Acid Red 92, C.I.45410, D&C Red No.28), Acid Red (Acid Red 52, C.I.45100), Lithol Rubine B (Pigment Red 57-1, C.I.15850, D&C Red No.6), Lithol Rubine BCA (Pigment Red 57, C.I.15850, D&C Red No.7), Lake Red CBA (Pigment Red 53(Ba), C.I.15585), Lithol Red (Pigment Red 49, C.I.15630), Deep Maroon (Pigment Red 63(Ca), C.I.15880, D&C Red No.34), Helindone Pink CN (Vat Red 1, C.I.73360, D&C Red No.30), Fast Acid Magenta (Acid Red 33, C.I.17200, D&C Red No.33), Permaton Red (Pigment Red 4, C.I.12085, D&C Red No.36), Eosine YS (Acid Red 87, C.I.45380, D&C Red No.22), Violamine R (Acid Violet 9, C.I.45190), Oil Red XO (Solvent Orange 7, C.I.12140), Tartrazine (Acid Yellow 23, C.I.19140, FD&C Yellow No.5), Sunset Yellow FCF (Acid Yellow 3, C.I.15985, FD&C Yellow No.6), Uranine (Acid Yellow 73, C.I.45350, D&C Yellow No.8), Quinoline Yellow WS (Acid Yellow 3, C.I.47005, D&C Yellow No.10), Quinoline Yellow SS (Solvent Yellow 33, C.I.47000, D&C Yellow No.11), Hanza Yellow (Pigment Yellow 1, C.I.11680), Brilliant Blue FCF 8Food Blue 2, C.I.42090, FD&C Blue No.1), Indigo Carmine (Acid Blue 74, C.I.73015, FD&C Blue No.2), Indigo (Vat Blue 1, C.I.73000), Phthalocyanine Blue(Pigment Blue 15, C.I.74160), Fast Green FCF (food Green 3, C.I.42053, FD&C Green No.3), Alizarine Cyanine Green (Acid Green 25, C.I.61570, D&C Green NO.5), Pyranine Conc (Solvent Green 7, C.I.59040, D&C Green NO.8), Light Green SF Yellowish (Acid, Green 5, C.I.42095), Dibromoiluorescein (Solvent Red 72, C.I.45370, D&C Orange NO.5), Permanent Orange (Pigment Orange 5, C.I.12075), Benzidine Orange G (Pigment Orange 13, C.I.21110), Diiodofluorescein (Solvent Red 73, C.I.45425, D&C Orange NO.10) and Erythrosine Yellowish NA (Acid red 95, C.I.45425, D&C Orange NO.11); as the natural coloring matter, carminic acid, laccaic acid, Safflower Red, brazilin and crocin, are mentioned. These powder can be mixed together and can be surface treated by oil, silicone or fluorine compound. These powder can be used alone or by combination at need.

A term of "a powder composition" of this invention means powder which can be obtained by mixing powder and copolymer dissolved in solvent and then by removing solvent or obtained by mixing powder and copolymer in dry condition, and the form of it is usually granule. The method to obtain the powder composition of this invention is not restricted, however, for instance, following methods can be mentioned. That is, the method to spray the solution of organic solvent such as butyl acetate, acetone or alcohol in which the copolymer is homogeneously dissolved to the powder, the method to coat the copolymer to the powder by adding the powder to said solution, after the agitation removing organic solvent, the method to bake said coated powder and the method to mix the copolymer and powder in a mixing apparatus i. e. a ball mill.

A term of "a powder dispersion in oil" means the dispersion which said powder is dispersed in oil, or the dispersion which the copolymer is dissolved or dispersed in oil and the powder is added and mixed, and the form of it is usually a liquid dispersion. The powder dispersion in oil of this invention can be obtained, for instance, by following methods. That is, the method to disperse the powder composition obtained by above mentioned method into ester oil or silicone oil, or to disperse or dissolve the copolymer into said oil, add the powder and mix using a mixing apparatus such as ball mill, bead mill and sand mill. Said powder dispersion in oil can be blend with cosmetic as it is.

Further, by containing (A) monomer into the copolymer of this invention, dispersing ability and stability of powder in oil can be improved. Amount of (A) monomer in the copolymer is bigger than 10% by weight (herein after shortened to %), desirably bigger than 15% and more desirably 20~99%.

Amount of copolymer in the powder composition and in powder dispersion in oil depends on a kind copolymer and is not limited, however, desirably bigger than 1% to the powder and more desirably bigger than 3%.

When the powder composition and/or powder dispersion in oil obtained as above are blended with cosmetic composition, the blending amount can be changed along with the state of product and is not restricted, however, the desirable region of blending amount of powder is 0.01~98% and more desirable region is 0.5~80%. If it is smaller than 0.01%, the effect in cosmetic is not sufficient. One kind or more kinds of these powder composition and powder dispersion in oil can be used alone or by combination.

To the cosmetic composition of this invention, solid, paste, soft solid and liquid oil, water, alcohols, water soluble polymer, film forming agent, surface active agent, oil soluble gelation agent, organic modified clay, resin, powder, UV absorbing agent, moisturizing agent, preservative, antimicrobial agent, perfume, salts, antioxydation agent, pH control agent, chelating agent, cooling agent, anti-inflammatory agent, skin care component (whitening agent, cell activator, skin improving agent, hematogenous agent, skin astringent, seborrheic agent etc), vitamins, amino acid, nucleic acid, hormone and inclusion compound which are used for an usual cosmetic can be added in the range which does not obstruct the effect of this invention.

As the examples of above mentioned additives are shown below, however not intended to be limited to them.

As the oil, natural animal or vegetables oil, semi-synthetic oil, hydrocarbon oil, higher fatty acid, higher fatty alcohol, ester oil, silicone oil, fluorine-containing oil can be mentioned.

As the natural animal or vegetables oil, or the semi-synthetic oil, avocado oil, linseed oil, almond oil, Chinese wax, perilla oil, olive oil, cacao butter, kapok oil, cajeput oil, carnauba wax, liver oil, candelilla wax, beef tallow, beef foot oil, beef bone fat, hydrogenated beef tallow, persic oil, whale oil, hydrogenated oil, wheat germ oil, sesami oil, rice germ oil, rice bran oil, sugarcone wax, sasanqua oil, safflower oil, shea butter, tung tree oil, cinnamon oil, shellac wax, turtle oil, soy beans oil, tea seed oil, camellia oil, primrose oil, corn oil, lard, rape-seed oil, paulownia oil, bran wax, germ oil, horse oil, persic oil, palm oil, palm germ oil, caster oil, hydrogenated caster oil, caster oil acid methylester, sunflower oil, grape oil, bayberry wax, jojoba oil, machademian nut oil, beeswax, mink oil, cotton seed oil, cotton wax, Japan tallow wax, Japan tallow germ wax, montan wax, coconut oil, hydrogenated coconut oil, tri coconut oil acid glyceride, sheep oil, peanut oil, lanolin, liquid lanolin, reduced lanolin, lanolic alcohol, hars lanolin, lanolin acetate, lanolic acid isopropyl, POE lanilic alcoholacetate, lanolic acid polyethylene glycol, POE hydrogenated lanolic alcoholether and yolk oil can be mentioned.

As the hydrocarbon oil, ozocerite, squalan, squalene, ceresin, paraffin, paraffin wax, liquid paraffin, pristane, polyisobutylene, microcrystalline wax and vaseline; as the higher fatty acid, lauric acid, myristic acid, palmitic acid, stearic acid, behenic acid, undecylenic acid, oleic acid, linoleic acid, linorenic acid, arachidonic acid, eicosapentaeic acid (EPA), docosahexaenic acid, isostearic acid and 12-hydroxystearic acid; as the higher fatty alcohol, lauric alcohol, myristyl alcohol, palmitic alcohol, stearyl alcohol, behenyl alcohol, hexadecyl alcohol, oleyl alcohol, isostearyl alcohol, hexyldodecanol, octyldodecanol, sedostearyl alcohol, 2-decyltetradecynol, cholesterol, phytosterol, POE cholesterol ether, monostearyl glycelinether (batyl alcohol) and monooleylglycelineether (serakyl alcohol) can be mentioned.

As the ester oil, diisobutyl adipate, 2-hexyldecyl adipate, di-2-heptylundecyl adipate, monoisostearic acid N-alkylglycol, isocetyl isostearate, triisostearic acid trimethylolpropane, cetyl 2-ethylhexanoate, di-2-ethylhexanoic acid ethyleneglycol, di-2-ethylhexanoic neopentylglycol, tri-2-ethylhexanoic acid trimethylol propane, tetra-2-ethylhexanoic acid pentaerythritol, cetyl octanoate, octyldodecyl rubber ester, oleyl oleate, octyldodecyl oleate, decyl oleate, di-caproic acid neopentylglycol, triethyl citrate, 2-ethylhexyl succinate, amyl acetate, ethyl acetate, butyl acetate, isocetyl stearate, butyl stearate, di-isopropyl sebacate, di-2-ethylhexyl sebacate, cetyl lactate, myristyl lactate, isopropyl palmitate, 2-ethylhexyl palmitate, 2-hexyldecyl palmitate, 2-heptylundecyl palmitate, cholesteryl 1,2-hydroxystearate, pentaerythritol fatty acid ester, isopropyl myristylate, 2-octyldodecyl myristylate, 2-hexyldecyl myristylate, myristyl myristylate, hexyldecyl dioctyloctanoate, ethyl laulate, hexyl laulate, N-lauroyl-L-glutamic acid-2-octyldodecylester and di-isostearyl malate can be mentioned.

As the glyceride oil, acetoglyceride, triisooctanoic acid glyceride, triisostearic acid glyceride, triisopalmitic acid glyceride, tri-2-ethylhexanoic acid glyceride, monostearic acid glyceride, di-2-heptylundecanoic acid glyceride and trimyristic acid glyceride can be mentioned.

As the silicone oil, dimethylpolysiloxane, methylphenylpolysiloxane, methylhydrogenpolysiloxane, octamethylcyclotetrasiloxane, decamethylcyclopentasiloxane, dodecamethylcyclopentasiloxane, tetramethyltetrahydrogen-cyclotetrasiloxane higher alkoxidenatured silicone such as stearoxy silicone, alkyl denatured silicone, higher fatty acid ester denatured silicone, higher fatty acid denatured silicone, fluoro denatured silicone, silicone resin and silicone rubber can be mentioned.

As the fluorine-containing oil, parfluoro polyether, parfluoro dekalin and parfluoro octane can be mentioned.

As the alcohol, lower fatty alcohol such as ethanol and isopropanol, sugar alcohol such as sorbitol and maltose can be mentioned and as the sterol, cholesterol, sitosterol, phytosterol and lanosterol can be mentioned.

As the water soluble polymer, a vegetable high polymer such as Arabian gum, tragacanth, galactan, locust bean gum, gua rubber, karaya gum, carrageenan, pectin, agar-agar, quince seed, starch (rice, cone, potato, wheat), sea weed extract, gum tragacanth, a microbial high polymer such as xanthane gum, dextran, succinoglycal and pullran, an animal high polymer such as collagen, casein, albumin and gelatin, starch high polymer such as carboxymethyl starch, methylhidroxypropyl satrch, cellulose high polymer such as methyl cellulose, ethyl cellulose, methylhydroxypropyl cellulose, carboxymethyl cellulose, hydroxypropyl cellulose, nitro cellulose, cellulose sodium sulfate, carboxymethyl cellulose, cryatalline cellulose and cellulose powder, alginic acid high polymer such as sodium alginate and alginic acid propyleneglycolester, vinyl high polymer such as polyvinylmethylether and carboxy vinyl polymer, polyoxyetylene high polymer, polyoxyethylene polyoxypropylene copolymer, acrylic polymer such as sodium polyacrylate, polyethylacrylate and polyacrylamide, inorganic water soluble high polymer such as polyethyleneimine, cationpolymer, bentonite, aluminium magnesium silicate, synthetic sodium magnesium silicate, hectolite and silicate unhydride can be mentioned.

Further, a film forming agent such as polyvinylalcohol and polyvinylpyrrolidone is contained in the additives.

In the surface active agent, there are anionic type, cationic type, nonionic type and amphoteric type. As the anionic type surface active agent, fatty acid soap such as sodium stearate and palmitic acid triethanolamine, alkylether carboxylic acid and salt, carboxylic acid salt which condensed amino acid and carboxylic acid, alkylsulfonic acid, alkenesulfonic acid, sulfonic acid salt of carboxylic acid ester, sulfonic acid salt of carboxylic acid amide, sulfonic acid salt of alkylsulfonic acid salt and it's formalin condensation, alkyl sulfonic acid ester salt, sulfonic acid ester of secondary fatty alcohol, sulfonic acid ester of alkyl and allyl ether, sulfonic acid ester salt of fatty acid ester, sulfonic acid ester salt of fatty acid alkylol amide, alkyl sulfonic acid ester salt of polyoxyethylene, sulfonic acid ester salt of turkey-red oil, alkyl phosphoric acid salt, ether phosphoric acid salt, alkyl allyl ether phosphoric acid salt, amide phosphoric acid salt and N-acyl amino acid can be mentioned.

As the cationic type surface active agent, alkyl amine salt, amine salt of polyamine and amino alcohol fatty acid derivatives, alkyl quaternary ammonium salt, aromatic quaternary ammonium salt, pyridinium salt and imidazolium salt can be mentioned.

As the nonionic type surface active agent, solbitane fatty acid ester, glycerin fatty acid ester, polyglycerin fatty acid ester, propyleneglycol fatty acid ester, polyethyleneglycol fatty acid ester, cane sugar fatty acid ester, polyoxyethylenealkylether, polyoxypropylenealkyl ether, polyoxyethylenealkylphenylether, polyoxyethylene fatty acid ester, polyoxyethylene sorbitane fatty acid ester, polyoxyethylene sorbitol fatty acid ester, polyoxyethyleneglycerin fatty acid ester, polyoxyethylenepropyleneglycol fatty acid ester, polyoxyethylene caster oil, polyoxyethylene hydrogenerated caster oil, polyoxyethylene phytostanol ether, polyoxyethylene phytosterol ether, polyoxyethylene chorestanol ether, polyoxyethylene choresteryl ether, polyoxyalkylene denatured organo polysiloxane, polyoxyalkylene alkyl denatured organo polysiloxane, alkanolamide, sugar ether and sugar amide can be mentioned.

As the amphoteric type surface active agent, betaine, amino carboxylic acid salt and imidazoline derivatives can be mentioned.

As the oil soluble gelating agent, metallic soap such as aluminum stearate, magnesium stearate and zinc myristate, amino acid derivatives such as N-lauroyl-L-glutamic acid, and α, γ-di-n-butylamine, dextrin fatty ester such as dextrin palmitic acid ester, dextrin stearic acid ester, dextrin 2-ethyl hexanoic acid palmitic ester, sugar fatty acid ester such as sugar palmitic ester, sugar stearic acid ester and benzylidene derivatives of sorbitol such as mono benzylidene sorbitol, di benzylidene sorbitol can be mentioned. Further, organic denatured clay such as dimethylbenzyldodecylammonium montmorillonite clay, dimethyloctadecylammonium, montmorillonite clay are included.

As the powder, for instance, filler, white pigment, colored pigment, organic powder, pearl agent and organic pigment can be mentioned. These kinds of powder can be combined or can be surface treated by oil, silicone or fluorine compound and one or more kinds of other powder can be blended at need.

As the ultra violet absorbing agent, benzoic acid U.V. absorbing agent such as para-amino benzoic acid, anthranilic acid U.V. absorbing agent such as methyl anthranilate, salicyclic acid U.V. absorbing agent such as methyl salicylate, cinnamic acid U.V absorbing agent such as octyl cinnamate, benzophenone U.V. absorbing agent such as 2,4-dihydroxybenzophenone and urocanic acid U.V absorbing agent such as ethyl urocanate can be mentioned.

As the moisturizing agent, sorbitol, xylitol, propyleneglycol, di- propyleneglycol, 1,3-butyleneglycol, glycerin, di-glycerin, polyethyleneglycol, hyaluronic acid, chondroitin sulfuric acid and pyrrolidone carboxylic acid can be mentioned.

As the preservative, paraoxybenzoic acid alkyl ester, benzoic acid, sodium benzoate, sorbitic acid, potassium sorbitate and phenoxyethanol can be mentioned. As the anti microbial agent, benzoic acid, salyciclic acid, carbolic acid, sorbitic acid, paraoxybenzoic acid ester, parachlorometacresol, hexachlorophene, chlorobenzalconium, chlorohexidine, trichlorocarbanilido, sensitizing dye and phenoxyethanol can be mentioned.

As the anti oxydation agent, tocopherol, butylhydroxyanisole and dibutylhydroxytoluene can be mentioned, and as the pH controlling agent, lactic acid, citric acid, glycolic acid, succinic acid, tartaric acid, di-malic acid, potassium carbonate, sodium hydrogen carbonate, ammonium hydrogen carbonate can be mentioned. As the chelate agent, alanine, sodium edetate, sodium polyphosphate, sodium metaphosphate and phospholic acid can be mentioned. As the refreshing agent, L-mentol and camphor, and as the anti inflammation agent, allantoin, glytil retin acid, tranexamic acid and azulene can be mentioned.

As the skin care component, skin whitening agent such as placenta extract, arbutin, glutathione and saxifragaceae extract, cell activation agent such as royal jelly, sensitizing dye, cholesterol derivatives and baby beef blood extract, damaged skin improving agent, hemotogeneous quickning agent such as nonylic acid valenylamide, nicotinic acid benzyl ester, nicotinic acid β-buthoxyethylester, capsaicin, gingerone, tincture of cantharis, ichthammol, caffeine, tannic acid, α-bomeol, nicotinic acid tocoferrol, inositol hexanicotinate, tolazoline, acetylcholine, cepharanthine, γ-oryzanol, skin astringent such as zinc oxide and tannic acid, anti seberrheic agent such as sulfur and thiamntholol can be mentioned.

As the vitamins, vitamin A such as vitamin A oil, retinol, retinol acetate or retinol palmitate, vitamin B2 such as liboflavin, liboflavin lactate or flavin adenine nucleotide, vitamin B6 such as pyridoxyne hydrochloric acid salt or pyridoxyne dioctanoate, vitamin C such as L-ascorbic acid, L-ascorbic acid dipalmitic acid ester, L-ascorbic acid-2-sodium sulphate or dl-α-tocoferol-L-ascorbic acid phosphoric acid diester dipotassium, pantothenic acid such as calcium panthothenate, D-panthotenyl alcohol, panthotenyl ethyl ether or acetyl panthotenyl ethyl ether, vitamin D such as ergocalciferol or cholecalciferol, nicotinic acids such as nicotinic acid, benzyl nicotinate or nicotinamide, vitamin E such as, dl-α-tocoferrol, dl-α-tocoferol acetate, dl-α-tocoferrol nicotinate and dl-α-tocoferol succinate, vitamin P and biotin can be mentioned.

Arginine, aspartic acid, cystine, cysteine, methionine, serine, leucine and tryptophane can be mentioned as the amino acid, dioxylibonucleo acid can be mentioned as the nucleic acid, and estradiol and ethynyl estradiol can be mentioned as the hormone.

In the present invention, term of cosmetic includes not only make up cosmetics such as foundation, pre-make up cream, cheek rouge, eye shadow, mascara, eye liner, eye blow, over coat agent and lip stick, skin care cosmetics such as lotion, milky lotion, cream, pack, massage agent, lip cream, hand cream and cleansing agent and hair care cosmetics, but also includes all kind of cosmetics applied to skin whose feeling to skin are very important. These can be widely used for any type of products such as an O/W type or W/O type emulsion form such as cream and lotion, an oil based solid cosmetics form such as lip stick, a paste form, a gelled form and a powder form.

EXAMPLES

The present invention will be understood more readily with reference to the following Examples, however, these Examples are intended to illustrate the invention and not to be construed to limit the scope of the invention. First of all, Examples for manufacturing of copolymer are illustrated.

Manufacturing Example 1

89 g of compound indicated by general formula (5), 10 g of N-vinylpyrrolidone, 1 g of 2-ethylhexyl acrylate, 100 g of toluene and 2 g of azobis(isobutyronitrile) are poured into a glass reactor with a thermometer and a reflux condenser, keep the temperature at 110~115° C. with constant stirring, reacted for 8 hours and accomplish the copolymerization reaction. After cooled, methanol is added to extract monomer residue, rinsed for several times and 94 g of viscose liquid product is obtained.

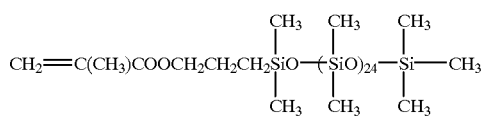

(5)

Manufacturing Example 2

75 g of compound indicated by general formula (6), 23 g of N-vinylpyrrolidone, 2 g of 2-ethylhexyl acrylate, 100 g of toluene and 2 g of azobis(isobutyronitrile) are poured into the same reactor to Manufacturing Example 1, and about 86 g of soft solid product is obtained by same procedure to Manufacturing Example 1.

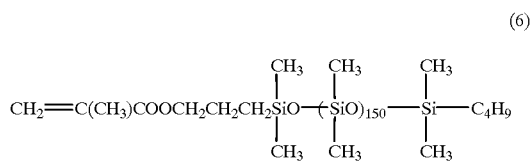

(6)

Manufacturing Example 3

69 g of compound indicated by general formula (5) used in Manufacturing Example 1, 11 g of N-vinylpyrrolidone, 15 g of stearyl methacrylate, 5 g of methyl methacrylate, 100 g of toluene and 2 g of azobis(isobutyronitrile) are used. By same procedure to Manufacturing Example 1, about 92 g of solid product is obtained.

Manufacturing Example 4

92 g of compound indicated by general formula (5) used in Manufacturing Example 1, 6 g of acrylamide, 2 g of styrene, 100 g of toluene and 2 g of azobis(isobutyronitrile) are used. By same procedure to Manufacturing Example 1, about 95 g of viscose liquid product is obtained.

Manufacturing Example 5

89 g of compound indicated by general formula (6) used in Manufacturing Example 2, 10 g of N-vinylpyrrolidone, 1 g of heptadecafluorodecyl methacrylate, 100 g of toluene and 2 g of azobis(isobutyronitrile) are used. By same procedure to Manufacturing Example 1, about 93 g of viscose liquid product is obtained.

Manufacturing Example 6

96 g of compound indicated by general formula (5) used in Manufacturing Example 1, 4 g of N-vinylacetoamide, 100 g of toluene and 2 g of azobis(isobutyronitrile) are used. By same procedure to Manufacturing Example 1, about 91 g of liquid product is obtained.

Manufacturing Example 7

75 g of compound indicated by general formula (5) used in Manufacturing Example 1, 20 g of compound indicated by general formula (7), 5 g of methyl methacrylate, 100 g of isopropanol and 2 g of azobis(isobutyronitrile) are used. By same procedure to Manufacturing Example 1 except keeping the reacting temperature at 80~85° C., about 94 g of soft solid product is obtained.

(7)

Manufacturing Example 8

75 g of compound indicated by general formula (6) used in Manufacturing Example 2, 15 g of compound indicated by general formula (8), 5 g of stearyl methacrylate, 5 g of methyl methacrylate, 100 g of isopropanol and 2 g of azobis(isobutyronitrile) are used. By same procedure to Manufacturing Example 7, about 86 g of liquid product is obtained.

(8)

Manufacturing Example 9

68 g of compound indicated by general formula (5) used in Manufacturing Example 1, 14 g of compound indicated by general formula (9), 14 g of N-vinylpyrrolidone, 4 g of methyl methacrylate, 100 g of toluene and 2 g of azobis (isobutyronitrile) are used. By same procedure to Manufacturing Example 1, about 90 g of solid product is obtained.

$$CH_2=C(CH_3)COO(C_3H_6O)_6H \qquad (9)$$

Manufacturing Example 10

87 g of compound indicated by general formula (10), 6 g of compound indicated by general formula (9) used in Manufacturing Example 9, 6 g of stearyl methacrylate, 1 of 2-ethylhexyl acrylate, 100 g of toluene and 2 g of azobis (isobutyronitrile) are used. By same procedure to Manufacturing Example 1, about 94 g of liquid product is obtained.

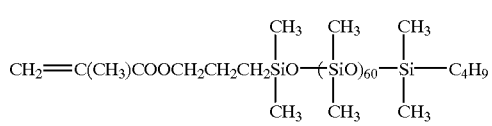

(10)

Manufacturing Example 11

68 g of compound indicated by general formula (6) used in Manufacturing Example 2, 14 g of compound indicated by general formula (9) used in Manufacturing Example 9, 14 g of stearyl methacrylate, 4 g of methyl methacrylate, 150 g of toluene and 2 g of azobis(isobutyronitrile) are used. By same procedure to Manufacturing Example 1, about 98 g of soft solid product is obtained.

Manufacturing Example 12

87 g of compound indicated by general formula (6) used in Manufacturing Example 2, 6 g of compound indicated by general formula (9) used in Manufacturing Example 9, 6 g of stearyl methacrylate, 1 g of heptadecafluorodecyl methacrylate, 100 g of toluene and 2 g of azobis (isobutyronitrile) are used. By same procedure to Manufacturing Example 1, about 95 g of liquid product is obtained.

Manufacturing Example 13

60 g of compound indicated by general formula (5) used in Manufacturing Example 1, 35 g of compound indicated by general formula (11), 5 g of methyl methacrylate, 100 g of toluene and 2 g of azobis(isobutyronitrile) are used. By same procedure to Manufacturing Example 1, about 94 g of soft solid product is obtained.

$$—CH_2=C(CH_3)COOCH_2CH_2O(C(=O)C_5H_{10}O)_3H—. \qquad (11)$$

Manufacturing Example 14

68 g of compound indicated by general formula (6) used in Manufacturing Example 2, 14 g of compound indicated by general formula (11) used in Manufacturing Example 13, 14 g of stearyl methacrylate, 4 g of methyl methacrylate, 11 g of toluene and 2 g of azobis(isobutyronitrile) are used. By same procedure to Manufacturing Example 1, about 96 g of soft solid product is obtained.

Manufacturing Example 15

68 g of compound indicated by general formula (5) used in Manufacturing Example 1, 14 g of compound indicated by general formula (51) used in Manufacturing Example 13, 14 g of N-vinylpyrrolidone, 4 g of methyl methacrylate, 100 g of toluene and 2 g of azobis(isobutyronitrile) are used. By same procedure to Manufacturing Example 1, about 88 g of viscose liquid product is obtained.

Manufacturing Example 16

64 g of compound indicated by general formula (5) used in Manufacturing Example 1, 35 g of compound indicated by general formula (11) used in Manufacturing Example 13, 1 g of heptadecafluorodecyl methacrylate, 100 g of toluene and 2 g of azobis(isobutyronitrile) are used. By same procedure to Manufacturing Example 1, about 93 g of soft solid product is obtained.

Manufacturing Example 17

92 g of compound indicated by general formula (5) used in Manufacturing Example 1, 5 g of compound indicated by general formula (12), 3 g of methyl methacrylate, 100 g of isopropanol and 2 g of azobis(isobutyronitrile) are used. By same procedure to the Manufacturing Example 7, 84 g of liquid product is obtained.

$$CH_2=C(CH_3)COO\ CH_2CH(OH)CH_3 \qquad (12)$$

Manufacturing Example 18

86 g of compound indicated by general formula (5) used in Manufacturing Example 1, 4 g of compound indicated by general formula (13), 5 g of stearyl methacrylate, 5 g of methyl methacrylate, 100 g of isopropanol and 2 g of azobis(isobutyronitrile) are used. By same procedure to Manufacturing Example 7, about 86 g of liquid product is obtained.

$$CH_2=CHCOOCH_2CH_2OH \qquad (13)$$

Manufacturing Example 19

82 g of compound indicated by general formula (6) used in Manufacturing Example 2, 4 g of compound indicated by general formula (14), 8 g of N-vinylpyrrolidone, 6 g of methyl methacrylate, 100 g of toluene and 2 g of azobis (isobutyronitrile) are used. By the same procedure to Manufacturing Example 1, about 86 g of liquid product is obtained.

$$CH_2=CHCOOCH_2CH(OH)CH_2 \qquad (14)$$

Manufacturing Example 20

72 g of compound indicated by general formula (10) used in Manufacturing Example 10, 8 g of compound indicated by general formula (12) used in Manufacturing Example 17, 12 g of stearyl methacrylate, 8 g of methyl methacrylate, 100 g of toluene and 2 g of azobis(isobutyronitrile) are used. By same procedure to Manufacturing Example 1, about 92 g of soft solid product is obtained.

Manufacturing Example 21

90 g of compound indicated by general formula (5) used in Manufacturing Example 1, 2 g of compound indicated by general formula (12) used in Manufacturing Example 17, 7 g of stearyl methacrylate, 1 g of heptadecafluorodecyl methacrylate, 150 g of isopropanol and 2 g of azobis (isobutyronitrile) are used. By same procedure to Manufacturing Example 7, about 97 g of liquid product is obtained.

Manufacturing Example 22

85 g of compound indicated by general formula (5) used in Manufacturing Example 1, 2 g of methacrylic acid, 13 g of methyl methacrylate, 100 g of isopropanol and 2 g of azobis(isobutyronitrile) are used. By same procedure to Manufacturing Example 7, about 94 g of liquid product is obtained.

Manufacturing Example 23

95 g of compound indicated by general formula (6) used in Manufacturing Example 2, 1 g of compound indicated by general formula (15), 4 g of methylmethacrylate, 100 g of butyl acetate and 2 g of azobis(isobutyronitrile) are used. By same procedure to Manufacturing Example 7, about 86 g of liquid product is obtained.

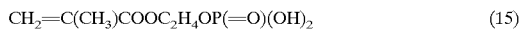

$$CH_2=C(CH_3)COOC_2H_4OP(=O)(OH)_2 \quad (15)$$

Manufacturing Example 24

96 g of compound indicated by general formula (5) used in Manufacturing Example 1, 1 g of compound indicated by general formula (16), 3 g of methyl methacrylate, 200 g of isopropanol and 2 g of azobis(isobutyronitrile) are used. By same procedure to Manufacturing Example 7, about 90 g of liquid product is obtained.

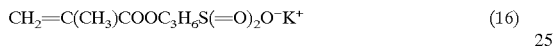

$$CH_2=C(CH_3)COOC_3H_6S(=O)_2O^-K^+ \quad (16)$$

Manufacturing Example 25

90 g of compound indicated by general formula (6) used in Manufacturing Example 2, 1 g of compound indicated by general formula (15) used in Manufacturing Example 23, 6 g of stearyl methacrylate, 3 g of methyl methacrylate, 100 g of butyl acetate and 2 g of azobis(isobutyronitrile) are used. By same procedure to Manufacturing Example 7, about 94 g of liquid product is obtained.

Manufacturing Example 26

75 g of compound indicated by general formula (6) used in Manufacturing Example 2, 1 g of methacrylic acid, 6 g of N-vinylpyrrolidone, 12 g of stearyl methacrylate, 6 g of 2-ethylhexylacrylate, 150 g of isopropanol and 2 g of azobis(isobutyronitrile) are used. By same procedure to Manufacturing Example 7, about 96 g of soft solid product is obtained.

Manufacturing Example 27

90 g of compound indicated by general formula (6) used in Manufacturing Example 2, 2 g of methacrylic acid, 7 g of stearyl methacrylate, 1 g of heptadecafluorodecyl methacrylate, 150 g of isopropanol and 2 g of azobis(isobutyronitrile) are used. By same procedure to Manufacturing Example 7, about 97 g of soft solid product is obtained.

As the second, Examples to prepare the powder compositions which use the copolymers manufactured by above mentioned Manufacturing Examples are illustrated.

Example 1

10 g of viscose liquid product of Manufacturing Example 1 is dissolved in 50 g of decamethylcyclopenta siloxane, add 40 g of titanium oxide (TaipecTTO-55(A); product of Ishihara Sangyo Co., Ltd.), then dispersed by a bead mill and titanium oxide dispersion (a-1) is obtained.

Example 2

5 g of soft solid product of Manufacturing Example 2 is dissolved in oil mixture of 20 g of decamethylcyclopenta siloxane and 15 g of tri-isooctanoic acid glyceryl, add 60 g of super fine particles of zinc oxide (ZnO-350; product of Sumitomo Osaka Cement Co., Ltd.), then dispersed by a bead mill and zinc oxide dispersion (a-2) is obtained.

Example 3

2 g of methylhydrogenepolysiloxane (KF-99; product of Shinetu Chemical Industries Co., Ltd.) is dissolved in methanol, after sprayed to 50 g of super fine particles of zinc oxide (ZnO-350; product of Sumitomo Osaka Cement Co., Ltd.) dried at 100 ° C. 8 g of soft solid of Manufacturing Example 2 is dissolved in 42 g of decamethylcyclopenta siloxane, add 50 g of said treated super fine particles of zinc oxide then dispersed by a bead mill and silicone treated zinc oxide dispersion (a-3) is obtained.

Example 4

5 g of solid product of Manufacturing Example 3 is dissolved in 45 g of decamethylcyclopentasiloxane, add 50 g of zinc oxide (Finex25; product of Sakai Chemical Co., Ltd.), then dispersed by a bead mill and zinc oxide dispersion (a-4) is obtained.

Example 5

0.5 g of dimethyldimethoxysilan (KBM-22; product of Shinetu Chemical Industries Co., Ltd.) is dissolved in methanol, after sprayed to 50 g of super fine particles of titanium oxide (TaipecTTO-55(A); product of Ishihara Sangyo Co., Ltd.) dried at 100° C. 10 g of viscose liquid product of Manufacturing Example 4 is dissolved in 50 g of decamethylcyclopentasiloxane, add 40 g of said treated titanium oxide then dispersed by a bead mill and alkoxysilan treated titanium oxide dispersion (a-5) is obtained.

Example 6

10 g of viscose liquid product of Manufacturing Example 5 is dissolved in 45 g of decamethylcyclopentasiloxane, add 40 g of titanium oxide (TaipecTTO-55(A); product of Ishihara Sangyo Co., Ltd.), then dispersed by a bead mill and titanium oxide dispersion (a-6) is obtained.

Example 7

8 g of liquid product of Manufacturing Example 6 is dissolved into 42 g of decamethylcyclopentasiloxane, add 50 g of zinc oxide (Finex25; product of Sakai Chemical Co., Ltd.), then dispersed by a bead mill and zinc oxide dispersion (a-7) is obtained.

Example 8

5 g of viscose liquid product of Manufacturing Example 1 is dissolved in 45 g of isopropanol, add 50 g of titanium oxide (TaipecTTO-55(A); product of Ishihara Sangyo Co., Ltd.) and dispersed, then solvent is distilled off and titanium oxide composition (a-8) is obtained.

Comparative Example 1

50 g of compound indicated by general formula (5) used in Manufacturing Example 1, 35 g of methyl methacrylate, 7.5 g of butyl methacrylate, 7.5 g of 2-ethylhexyl acrylate, 100 g of toluene and 2 g of azobis(isobutyronitrile) are used. By same procedure to Manufacturing Example 1, about 95 g of solid product is obtained.

4 g of this solid product is dissolved in 46 g of decamethylcyclopentasiloxane, add 50 g of titanium-oxide TaipecTTO-55(A); product of Ishihara Sangyo Co., Ltd.), then dispersed by a bead mill and titanium oxide dispersion (a-9) is obtained.

Example 9

10 g of soft solid product of Manufacturing Example 7 is dissolved in 50 g of decamethylcyclopentasiloxane, add 40 g of titanium oxide (TaipecTTO-55(A) product of Ishihara Sangyo Co., Ltd.), then dispersed by a bead mill and titanium oxide dispersion (b-1) is obtained.

Example 10

8 g of liquid product of Manufacturing Example 8 is mixed with 42 g of decamethylcyclopentasiloxane, add 50 g of zinc oxide (Finex25; product of Sakai Chemical Co., Ltd.), then dispersed by a bead mill and zinc oxide dispersion (b-2) is obtained.

Example 11

12 g of solid product of Manufacturing Example 9 is dissolved in the mixture of 27.5 g of decamethylcyclopentasiloxane and 12.5 g of tri-isooctanoic acid glyceryl, add 50 g of zinc oxide (Finex25; product of Sakai Chemical Co., Ltd.), then dispersed by a bead mill and zinc oxide dispersion (b-3) is obtained.

Example 12

8 g of liquid product of Manufacturing Example 10 is mixed with 42 g of decamethylcyclopentasiloxane, add 50 g of titanium oxide (TaipecTTO-55(A); product of Ishihara Sangyo Co., Ltd.), then dispersed by a bead mill and titanium oxide dispersion (b-4) is obtained.

Example 13

0.5 g of n-decyltrimethoxysilan (KBM-3103; product of Shinetu Chemical Industries Co., Ltd.) is dissolved in methanol, after sprayed to 50 g of super fine particles of zinc oxide (ZnO-350; product of Sumitomo Osaka Cement Co., Ltd.) dried at 100° C. 4 g of liquid product of Manufacturing Example 10 is mixed with 46 g of decamethylcyclopentasiloxane, add 50 g of said treated super fine particles of zinc oxide then dispersed by a bead mill and alkoxysilan treated zinc oxide dispersion (b-5) is obtained.

Example 14

8 g of soft solid product of Manufacturing Example 11 is dissolved in 42 g of decamethylcyclopentasiloxane, add 50 g of zinc oxide (Finex25; product of Sakai Chemical Co., Ltd.), then dispersed by a bead mill and zinc oxide dispersion (b-6) is obtained.

Example 15

8 g of soft solid product of Manufacturing Example 11 is dissolved in 52 g of decamethylcyclopenta-siloxane, add 40 g of stearic acid treated titanium oxide (TipecTTO-S-2; product of Ishihara Sangyo Co., Ltd.), then dispersed by a bead mill and stearic acid treated titanium oxide dispersion (b-7) is obtained.

Example 16

0.5 g of n-decyltrimethoxysilan (KBM-3103; product of Shinetu Chemical Industries Co., Ltd.) is dissolved in methanol, after sprayed to 50 g of super fine particles of zinc oxide (ZnO-350; product of Sumitomo Osaka Cement Co., Ltd.) dried at 100° C. 8 g of soft solid product of Manufacturing Example 11 is dissolved in 42 g of decamethylcyclopentasiloxane, add 50 g of said treated super fine particles of zinc oxide then dispersed by a bead mill and alkoxysilan treated zinc oxide dispersion (b-8) is obtained.

Example 17

2 g of methylhydrogenepolysiloxane (KF-99; product of Shinetu Chemical Industries Co., Ltd.) is dissolved in methanol, after sprayed to 50 g of zinc oxide (ZnO-350; product of Sumitomo Osaka Cement Co., Ltd.) dried at 100° C. 8 g of soft solid product of Manufacturing Example 11 is dissolved in 42 g of decamethylcyclopentasiloxane, add 50 g of said treated zinc oxide then dispersed by a bead mill and silicone treated zinc oxide dispersion (b-9) is obtained.

Example 18

0.5 g of dimethyldimethoxysilan (KBM-22; product of Shinetu Chemical Industries Co., Ltd.) is dissolved in methanol, after sprayed to 50 g of titanium oxide (TaipecTTO-55(A); product of Ishihara Sangyo Co., Ltd.) dried at 100° C. 10 g of liquid product of Manufacturing Example 12 is dissolved in 50 g of decamethylcyclopentasiloxane, add 40 g of said treated titanium oxide then dispersed by a bead mill and alkoxysilan treated titanium oxide dispersion (b-10) is obtained.

Example 19

5 g of soft solid product of Manufacturing Example 11 is dissolved in 45 g of isopropanol, add 50 g of titanium oxide (TaipecTTO-55(A); product of Ishihara Sangyo Co., Ltd.) and dispersed, then solvent is distilled off and titanium oxide composition (b-11) is obtained.

Comparative Example 2

8 g of the solid product obtained in Comparative Example 1 is dissolved in 52 g of decamethylcyclopentasiloxane, add 40 g of titanium oxide (TaipecTTO-55(A); product of Ishihara Sangyo Co., Ltd.), then dispersed by a bead mill and titanium oxide dispersion (b-12) is obtained.

Example 20

0.5 g of dimethyldimethoxysilan (KBM-22; product of Shinetu Chemical Industries Co., Ltd.) is dissolved in methanol, after sprayed to 50 g of titanium oxide (TaipecTTO-55(A); product of Ishihara Sangyo Co., Ltd.) dried at 100° C. 8 g of soft solid product of Manufacturing Example 13 is dissolved in 52 g of decamethylcyclopentasiloxane, add 40 g of said treated titanium oxide then dispersed by a bead mill and alkoxysilan treated titanium oxide dispersion (c-1) is obtained.

Example 21

0.5 g of n-decyltrimethoxysilan (KBM-3103; product of Shinetu Chemical Industries Co., Ltd.) is dissolved in methanol, after sprayed to 50 g of super fine particles of zinc oxide (ZnO-350; product of Sumitomo Osaka Cement Co., Ltd.) dried at 100° C. 5 g of soft solid product of Manufacturing Example 14 is dissolved in 55 g of decamethylcyclopentasiloxane, add 40 g of said treated super fine particles of zinc oxide then dispersed by a bead mill and alkoxysilan treated zinc oxide dispersion (c-2) is obtained.

Example 22

2 g of methylhydrogenepolysiloxane (KF-99; product of Shinetu Chemical Industries Co., Ltd.) is dissolved in methanol, after sprayed to 50 g of super fine particles of zinc oxide (ZnO-350; product of Sumitomo Osaka Cement Co., Ltd.) dried at 100° C. 8 g of soft solid product of Manufacturing Example 14 is dissolved in 42 g of decamethylcyclopentasiloxane, add 50 g of said treated super fine particles of zinc oxide then dispersed by a bead mill and silicone treated zinc oxide dispersion (c-3) is obtained.

Example 23

0.5 g of dimethyldimethoxysilan (KBM-22; product of Shinetu Chemical Industries Co., Ltd.) is dissolved in methanol, after sprayed to 50 g of zinc oxide (Finex25; product of Sakai Chemical Co., Ltd.) dried at 100° C. 5 g of soft solid product of Manufacturing Example 14 is dissolved in the mixture of 20 g of decamethylcyclopentasiloxane and 15 g of tri-isooctanoic acid glyceryl, add 60 g of said treated zinc oxide then dispersed by a bead mill and zinc oxide dispersion (c4) is obtained.

Example 24

10 g of viscose liquid product of Manufacturing Example 15 is dissolved in 50 g of decamethylcyclopentasiloxane, add 40 g of zinc oxide (Finex25; product of Sakai Chemical Co., Ltd.), then dispersed by a bead mill and zinc oxide dispersion (c-5) is obtained.

Example 25

0.5 g of dimethyldimethoxysilan (KBM-22; product of Shinetu Chemical Industries Co., Ltd.) is dissolved in methanol, after sprayed to 50 g of titanium oxide (TaipecTTO-55(A); product of Ishihara Sangyo Co., Ltd.) dried at 100° C. 10 g of soft solid product of Manufacturing Example 16 is dissolved in 50 g of decamethylcyclopentasiloxane, add 40 g of said treated titanium oxide then dispersed by a bead mill and alkoxysilan treated titanium oxide dispersion (c-6) is obtained.

Example 26

5 g of viscose liquid product of Manufacturing Example 15 is dissolved in 45 g of isopropanol, add 50 g of titanium oxide (TaipecTTO-55(A); product of Ishihara Sangyo Co., Ltd.) and dispersed, then solvent is distilled off and titanium oxide composition (c-7) is obtained.

Example 27

10 g of liquid product of Manufacturing Example 17 is mixed with 50 g of decamethylcyclopentasiloxane, add 40 g of titanium oxide (TaipecTTO-55(A); product of Ishihara Sangyo Co., Ltd.), then dispersed by a bead mill, and titanium oxide dispersion (d-1) is obtained.

Example 28

8 g of liquid product of Manufacturing Example 18 is mixed with 42 g of decamethylcyclopentasiloxane, add 50 g of zinc oxide (Finex25; product of Sakai Chemical Co., Ltd.), then and dispersed by a bead mill, and zinc oxide dispersion (d-2) is obtained.

Example 29

0.5 g of n-decyltrimethoxysilan (KBM-3103; product of Shinetu Chemical Industries Co., Ltd.) is dissolved in methanol, after sprayed to 50 g of zinc oxide (Finex25; product of Sakai Chemical Co., Ltd.) dried at 100° C. 8 g of liquid product of Manufacturing Example 18 is mixed with 42 g of decamethylcyclopentasiloxane, add 50 g of said treated zinc oxide then dispersed by a bead mill and alkoxysilan treated zinc oxide dispersion (d-3) is obtained.

Example 30

8 g of liquid product of Manufacturing Example 18 is mixed with 52 g of decamethylcyclopentasiloxane, add 40 g of stearic acid treated titanium oxide (TaipecTTO-S-2; product of Ishihara Sangyo Co., Ltd.), then dispersed by a bead mill, and stearic acid treated titanium oxide dispersion (d-4) is obtained.

Example 31

2 g of methylhydrogenepolysiloxane (KF-99; product of Shinetu Chemical Industries Co., Ltd.) is dissolved in methanol, after sprayed to 50 g of super fine particles of zinc oxide (ZnO-350; product of Sumitomo Osaka Cement Co., Ltd.) dried at 100° C. 8 g of liquid product of Manufacturing Example 18 is dissolved in 42 g of decamethylcyclopentasiloxane, add 50 g of said treated super fine particles of zinc oxide then dispersed by a bead mill and silicone treated zinc oxide dispersion (d-5) is obtained.

Example 32

12 g of liquid product of Manufacturing Example 19 is dissolved in 48 g of decamethylcyclopentasiloxane, add 40 g of zinc oxide (Finex25; product of Sakai Chemical Co., Ltd.), then dispersed by a bead mill, and zinc oxide dispersion (d-6) is obtained.

Example 33

8 g of soft solid product of Manufacturing Example 20 is dissolved in 42 g of decamethylcyclopentasiloxane, add 50 g of titanium oxide (TaipecTTO-55(A); product of Ishihara Sangyo Co., Ltd.), then dispersed, and titanium oxide dispersion (d-7) is obtained.

Example 34

0.5 g of n-decyltrimethoxysilan (KBM-3103; product of Shinetu Chemical Industries Co., Ltd.) is dissolved in methanol, after sprayed to 50 g of super fine particles of zinc oxide (ZnO-350; product of Sumitomo Osaka Cement Co., Ltd.) dried at 100° C. 5 g of soft solid product of Manufacturing Example 20 is dissolved in the mixture of 20 g of decamethylcyclopentasiloxane and 15 g of tri-isooctanoic acid glyceryl, add 60 g of said treated super fine particles of zinc oxide then dispersed by a bead mill and alkoxysilan treated zinc oxide dispersion (d-8) is obtained.

Example 35

0.5 g of dimethyldimethoxysilan (KBM-22; product of Shinetu Chemical Industries Co., Ltd.) is dissolved in methanol, after sprayed to 50 g of titanium oxide (TaipecTTO-55(A); product of Ishihara Sangyo Co., Ltd.) dried at 100° C. 10 g of liquid product of Manufacturing Example 21 is dissolved in 50 g of decamethylcyclopentasiloxane, add 40 g of said treated titanium oxide then dispersed by a bead mill and alkoxysilan treated titanium oxide dispersion (d-9) is obtained.

Example 36

5 g of soft solid product of Manufacturing Example 20 is dissolved in 45 g of isopropanol, add 50 g of titanium oxide (TaipecTTO-55(A); product of Ishihara Sangyo Co., Ltd.) and dispersed, then solvent is distilled off and titanium oxide composition (d-10) is obtained.

Example 37

10 g of liquid product of Manufacturing Example 22 is dissolved in 50 g of decamethylcyclopentasiloxane, add 40 g of titanium oxide (TaipecTTO-55(A); product of Ishihara Sangyo Co., Ltd.), then dispersed, and titanium oxide dispersion (e-1) is obtained.

Example 38

8 g of liquid product of Manufacturing Example 23 is mixed with 42 g of decamethylcyclopentasiloxane, add 50 g of zinc oxide (Finex25; product of Sakai Chemical Co., Ltd.), then dispersed by a bead mill, and zinc oxide dispersion (e-2) is obtained.

Example 39

10 g of liquid product of Manufacturing Example 24 is dissolved in the mixture of 27.5 g of decamethylcyclopentasiloxane and 12.5 g of tri-isooctanoic acid glyceryl, add 50 g of zinc oxide (Finex25; product of Sakai Chemical Co., Ltd.), then dispersed by a bead mill, and zinc oxide dispersion (e-3) is obtained.

Example 40

8 g of liquid product of Manufacturing Example 25 is mixed with 42 g of decamethylcyclopentasiloxane, add 50 g of titanium oxide (TaipecTTO-55(A); product of Ishihara Sangyo Co., Ltd.), then dispersed by a bead mill, and titanium oxide dispersion (e-4) is obtained.

Example 41

0.5 g of n-decyltrimethoxysilan (KBM-3103; product of Shinetu Chemical Industries Co., Ltd.) is dissolved in methanol, after sprayed to 50 g of super fine particles of zinc oxide (ZnO-350; product of Sumitomo Osaka Cement Co., Ltd.) dried at 100° C. 4 g of liquid product of Manufacturing Example 25 is mixed with 46 g of decamethylcyclopentasiloxane, add 50 g of said treated super fine particles of zinc oxide then dispersed by a bead mill and alkoxysilan treated zinc oxide dispersion (e-5) is obtained.

Example 42

8 g of soft solid product of Manufacturing Example 26 is dissolved in 42 g of decamethylcyclopentasiloxane, add 50 g of zinc oxide (Finex25; product of Sakai Chemical Co., Ltd.), then dispersed by a bead mill, and zinc oxide dispersion (e-6) is obtained.

Example 43

8 g of soft solid product of Manufacturing Example 26 is dissolved in 52 g of decamethylcyclopentasiloxane, add 40 g of stearic acid treated titanium oxide (TaipecTTO-S-2; product of Ishihara Sangyo Co., Ltd.), then dispersed by a bead mill, and stearic acid treated titanium oxide dispersion (e-7) is obtained.

Example 44

0.5 g of n-decyltrimethoxysilan (KBM-3103; product of Shinetu Chemical Industries Co., Ltd.) is dissolved in methanol, after sprayed to 50 g of zinc oxide (Finex25; product of Sakai Chemical Co., Ltd.) dried at 100° C. 8 g of soft solid product of Manufacturing Example 26 is dissolved in 42 g of decamethylcyclopentasiloxane, add 50 g of said treated zinc oxide then dispersed by a bead mill and alkoxysilan treated zinc oxide dispersion (e-8) is obtained.

Example 45

2 g of methylhydrogenepolysiloxane (KF-99; product of Shinetu Chemical Industries Co., Ltd.) is dissolved in methanol, after sprayed to 50 g of super fine particles of zinc oxide (ZnO-350; product of Sumitomo Osaka Cement Co., Ltd.) dried at 100° C. 8 g of soft solid product of Manufacturing Example 26 is dissolved in 42 g of decamethylcyclopentasiloxane, add 50 g of said treated super fine particles of zinc oxide then dispersed by a bead mill and silicone treated zinc oxide dispersion (e-9) is obtained.

Example 46

0.5 g of dimethyldimethoxysilan (KBM-22; product of Shinetu Chemical Industries Co., Ltd.) is dissolved in methanol, after sprayed to 50 g of titanium oxide (TaipecTTO-55(A); product of Ishihara Sangyo Co., Ltd.) dried at 100° C. 10 g of liquid product of Manufacturing Example 27 is dissolved in 50 g of decamethylcyclopentasiloxane, add 40 g of said treated titanium oxide then dispersed by a bead mill and alkoxysilan treated titanium oxide dispersion (e-10) is obtained.

Example 47

5 g of soft solid product of Manufacturing Example 26 is dissolved in 45 g of isopropanol, add 50 g of titanium oxide (TaipecTTO-55(A); product of Ishihara Sangyo Co., Ltd.) dispersed, and solvent is distilled off, thus the titanium oxide composition (e-11) is obtained.

(Evaluation of Dispersing Ability)

Each powder composition and powder dispersion in oil of Example 1~47 and Comparative Example 1~2 is mixed with decamethylcyclopentasiloxane so as the concentration of powder to be 5%, and these dispersion samples are observed by an optical microscope (magnification; 100) and the state of each dispersion samples are inspected. According to the results by microscopic picture inspection, the specimen of Example 1~47 cohesion of powder particles are very few and have very good dispersing ability. On the contrary, the dispersing ability of samples of Comparative Example 1 and 2 are not good.

Example 48~94 and Comparative Example 3~6

(Sun Screening Cream)

Sun screening creams of component listed in Table 1 to Table 6 are prepared and the quality are evaluated.

(Preparation Method)

Table 1

A: Component 7~9 are mixed homogeneously.
B: After component 1~6 are heated and homogenized, A is added and emulsified.
C: Component 10, 11~18 are added to B and sun screening creams are obtained.

Table 2

A: Components 7~9 are mixed homogeneously.
B: Components 1~6 are heated and homogenized, then A is added and emulsified.

C: Component 10, 11~21 are added to B and sun screening creams are obtained.

Table 3 (product of Comparative Example 3 is same as to the product of Table 1)

A: Components 7~9 are mixed homogeneously.
B: Components 1~6 are heated and homogenized, then A is added and emulsified.
C: Component 10, 11~17 are added to B and sun screening creams are obtained.

Table 4 product of Comparative Example 4 is same as to the product of Table 2)

A: Components 7~9 are mixed homogeneously.
B: Components 1~6 are heated and homogenized, then A is added and emulsified.
C: Component 10, 11~12 are added to B and sun screening creams are obtained.

Table 5 product of Comparative Example 4 is same as to the product of Table 2)

A: Components 7~9 are mixed homogeneously.
B: Components 1~6 are heated and homogenized, then A is added and emulsified.
C: Component 10, 11~21 are added to B and sun screening creams are obtained.

Table 6

A: Components 7~9 are mixed homogeneously.
B : Components 1-6 are heated and component 11~17 are added and homogenized, then A is added and emulsified.
C: Component 10 is added to B and sun screening creams are obtained.

The evaluation of quality in Table 1 and Table 6 are carried out as follows.

1. Dispersing Stability of Powder

The prepared sun screening cream is placed at room temperature for 4 weeks, then the cohering of powder is observed. Evaluated levels are illustrated below.
[Evaluation Standard]
  ◎: no cohesion of powder is observed
  ○: powder is slightly cohered
  △: cohered
  ×: cohesion is clearly observed 2. Feeling at Actual Use Evaluated by 30 special panels and regarding following items, that is, dry feeling upon use, well spreading, transparency of cosmetic film, non sticky feeling after used, smoothness, fresh feeling upon use and effect of sun screening are evaluated. Evaluation is carried out by 5 steps along with following standard and averaged.
[Evaluation Standard]
  5 points: excellent
  4 points: good
  3 points: normal
  2 points: slightly bad
  1 point: bad
[Judgement]
  ◎: higher than 4.5 points
  ○: higher than 3.5 less than 4.5
  △: higher than 2.5 less than 3.5
  ×: less than 2.5 points As be obvious from the results of Table 1~Table 6, cohesive of powder is not observed on the products of each Examples of this invention and the dispersion stability of these products are excellent. Regarding the feeling of each Examples at actual use are very good, and these products can be said to have both excellent stability and feeling. On the contrary, powder dispersion of the products of Comparative Examples 5 and 6 which are blended with untreated powder or the conventional silicone treated powder is not good and the feeling at the actual use is not sufficient. Further, regarding to the products of Comparative Example 3 and 4, slight cohesion of powder is observed, the transparency of cosmetic film inferiors to that of this invention, and the feeling at actual use is not sufficient compared with that of this invention.

Example 95

(Sun Screening W/O Milky Lotion)

| (component) | (%) |
|---|---|
| 1. tri-isooctanoic acid glyceryl | 5.0 |
| 2. dimethylpolysiloxan (10 cSt) | 4.0 |
| 3. decamethylcyclopentasiloxane | 8.0 |
| 4. 2-ethylhexyl para-mitoxycinnamate | 5.0 |
| 5. copolymer of polyoxyethylene.methylpolysiloxane(*1) | 1.0 |
| 6. 1,3-butylene glycol | 4.0 |
| 7. preservative | quantum sufficit |
| 8. refined water | balance |
| 9. perfume | quantum sufficit |
| 10. zinc oxide dispersion of Example 4(*2) | 35.0 |
| 11. titanium oxide dispersion of Example 5(*3) | 20.0 |

(*1): silicone KF-6017 (product of Sinetsu Chemical Industries Co., Ltd.)
(*2): zinc oxide dispersion of Example 14, 22, 28 or 41 can be used instead of Example 4.
(*3): titanium oxide dispersion of Example 15, 20, 30 or 43 can be used instead of Example 5.

(Preparation Method)
A: Components 6~8 are mixed homogeneously.
B: Components 1~5 are heated, then A is added and emulsified.
C: Component 9~11 is added to B and sun screening W/O milky lotion is obtained.

Sun screening W/O milky lotion in which powder does not cohere, have a good dispersion stability, well spreadable onto skin, smooth and lack of stickiness after application, have a good transparency, natural appearance and have a good endurance of make-up can be obtained.

Example 96

(Pre Make-up Cream)

| (component) | (%) |
|---|---|
| 1. neopentylglycol dicaprate | 3.0 |
| 2. pentaerythritol resinate | 0.5 |
| 3. decamethylcyclopentasiloxane | 8.0 |
| 4. 2-ethylhexyl para-mitoxycinnamate | 5.0 |
| 5. copolymer of polyoxyethylene.methylpolysiloxane(*1) | 2.0 |
| 6. 1,3-butylene glycol | 4.0 |
| 7. ethanol | 2.5 |
| 8. preservative | quantum sufficit |
| 9. refined water | balance |
| 10. perfume | quantum sufficit |

-continued

| (component) | (%) |
|---|---|
| 11. nylon powder | 10.0 |
| 12. zinc oxide dispersion of Example 7(*2) | 35.0 |

(*1): silicone KF-6017 (product of Sinetsu Chemical Industries Co., Ltd.)
(*2): zinc oxide dispersion of Example 11, 24, 29 or 39 can be used instead of Example 7.

(Preparation Method)
A: Components 6~9 are mixed homogeneously.
B: Components 1~5 are heated, then components 11, 12 are added.
C: A is added to B and emulsified, then component 10 is added and a pre make-up cream is obtained.

In obtained pre make-up cream powder does not cohesive and have a good dispersion stability, well spreadable onto skin, smooth and lack of stickiness after application, have a good transparency, natural appearance and have a good endurance of make-up.

Example 97
(Foundation)

| (component) | (%) |
|---|---|
| 1. ceresine wax | 5.0 |
| 2. microcrystalline wax | 1.0 |
| 3. liquid paraffin | 4.0 |
| 4. tri-isooctanoic acid glyceryl | 3.0 |
| 5. dimethylpolysiloxane (6cSt) | 20.0 |
| 6. copolymer of methylpolysiloxane.cetylmethyl-polysiloxane.poly(oxyetylene.oxypropylene)methylpolysiloxane | 2.0 |
| 7. 1,3-butylene glycol | 8.0 |
| 8. preservative | quantum sufficit |
| 9. refined water | balance |
| 10. perfume | quantum sufficit |
| 11. powder dispersion (*1) | 17.0 |
| (*1) powder dispersion | |
| a. titanium oxide | 50.8 |
| b. red iron oxide | 1.0 |
| c. yellow iron oxide | 6.8 |
| d. black iron oxide | 1.4 |
| e. copolymer of Manufacturing Example 2(*2) | 10.0 |
| f. decamethylcyclopentasiloxan | 30.0 |

(*2): copolymer of Example 8, 18, or 23 can be used instead of copolymer of Manufacturing Example 2.

(Preparation Method)
A: 0.6 g of n-decyltrimethoxysilan(KBM-3103; product of Shinetu Chemical Industries Co., ltd.) is dissolved in methanol, sprayed to component a~d, then dried at 100° C.
B: Component e is dissolved in f and add A and dispersed by bead mill and powder dispersion of component 11 is obtained.
C: Components 7~9 are mixed homogeneously.
D: Components 1~6 are heated, then C is added and emulsified.
E: B and component 10 is added to D and a foundation is obtained.

A foundation in which powder does not cohesive, have a good dispersion stability, well spreadable onto skin, smooth and lack of stickiness after application, have a good transparency, natural appearance and have a good endurance of make-up can be obtained.

Example 98
(Foundation)

| (component) | (%) |
|---|---|
| 1. ceresine wax | 5.0 |
| 2. microcrystalline wax | 1.0 |
| 3. liquid parafin | 4.0 |
| 4. tri-isooctanoic acid glyceryl | 3.0 |
| 5. dimethylpolysiloxane (6cSt) | 20.0 |
| 6. copolymer of methylpolysiloxane.cetylmethyl-polysiloxane.poly(oxyetylene.oxypropylene)methylpolysiloxane | 2.0 |
| 7. 1,3-butylene glycol | 8.0 |
| 8. preservative | quantum sufficit |
| 9. refined water | balance |
| 10. perfume | quantum sufficit |
| 11. powder composition (*1) | 11.9 |
| 12. decamethylcyclopentasiloxane | 5.1 |
| (*1) powder composition | |
| a. titanium oxide | 50.8 |
| b. red iron oxide | 1.0 |
| c. yellow iron oxide | 6.8 |
| d. black iron oxide | 1.4 |
| e. copolymer of Manufacturing Example 1(*2) | 10.0 |

(*2): copolymer of Example 11, 13, 20 or 26 can be used instead of copolymer of Manufacturing Example 1.

(Preparation Method)
A: Component e is dissolved in 50 g of isopropanol, add components a~d and mixed, solvent is distilled off and powder composition 11 is obtained. And dispersed in component 12.
B: Components 7~9 are mixed homogeneously.
C: Components 1~6 are heated, then B is added and emulsified.
D: A and component 10 is added to C and a foundation is obtained.

A foundation in which powder does not cohesive, have a good dispersion stability, well spreadable onto skin, smooth and lack of stickiness after application, have a good transparency, natural appearance and have a good endurance of make-up can be obtained.

Example 99
(Foundation)

| (component) | (%) |
|---|---|
| 1. ceresine wax | 5.0 |
| 2. microcrystalline wax | 1.0 |
| 3. liquid parafin | 4.0 |
| 4. tri-isooctanoic acid glyceryl | 3.0 |
| 5. dimethylpolysiloxane (6cSt) | 20.0 |
| 6. copolymer of methylpolysiloxane.cetylmethyl-polysiloxane.poly(oxyetylene.oxypropylene)methylpolysiloxane | 2.0 |
| 7. 1,3-butylene glycol | 8.0 |
| 8. preservative | quantum sufficit |
| 9. refined water | balance |
| 10. perfume | quantum sufficit |
| 11. powder dispersion (*1) | 17.0 |
| 12. powder dispersion (*2) | 10.0 |
| (*1) powder dispersion | |
| a. silicone treated titanium oxide | 50.8 |
| b. silicone treated red iron oxide | 1.0 |

-continued

| (component) | (%) |
|---|---|
| c. silicone treated yellow iron oxide | 6.8 |
| d. silicone treated black iron oxide | 1.4 |
| e. copolymer of Manufacturing Example 2(*3) | 10.0 |
| f. decamethylcyclopentasiloxane | 30.0 |
| (*2) powder dispersion | |
| g. teflon treated talk | 50.0 |
| h. copolymer of Manufacturing Example 5(*4) | 8.0 |
| i. decamethylcyclopentasiloxane | 42.0 |

(*3): copolymer of Example 10, 14, 19 or 24 can be used instead of copolymer of Manufacturing Example 2.
(*4): copolymer of Example 12, 16, 21 or 27 can be used instead of copolymer of Manufacturing Example 5.

(Preparation Method)
A: Component e is dissolved in component f, add components a~d and dispersed by a bead mill, and powder dispersion 11 is obtained.
B: Component h is dissolved in component i, add components g and dispersed by a bead mill, and powder composition 12 is obtained.
C: Components 7~9 are mixed homogeneously.
D: Components 1~6 are heated, then B is added and emulsified.
E: A, B and component 10 is added to D and a foundation is obtained.

A foundation in which powder does not cohesive, have a good dispersion stability, well spreadable onto skin, smooth and lack of stickiness after application, have a good transparency, natural appearance and have a good endurance of make-up can be obtained.

[Effect of the Invention]

As above mentioned, since the powder composition and the powder dispersion in oil of this invention uses a copolymer containing an organo polysiloxane monomer and a monomer containing nitrogen group, a monomer possessing a polyoxyalkylene group, a monomer possessing a polylactone group, a monomer possessing a hydroxyl group or a monomer possessing an anionic group as the components for the treatment of powder, have a less cohesive tendency and is superior in a dispersing ability and a dispersion stability. Further, the cosmetic composition which contains them gives an excellent sensation at the actual use and has an excellent quality as a consumer's goods.

TABLE 1

| | Example | | | | | | | C.E. |
|---|---|---|---|---|---|---|---|---|
| component (%) | 48 | 49 | 50 | 51 | 52 | 53 | 54 | 3 |
| 1. triisooctanoic acid glyceryl | 5 | — | 5 | 5 | 5 | 5 | 5 | 5 |
| 2. dimethylpolysiloxane (6cSt) | 5 | 5 | 5 | 5 | 5 | 5 | 5 | 5 |
| 3. decamethylcyclopentasiloxane | — | 20 | 10 | 10 | — | — | 10 | 10 |
| 4. 2-ethylhexyl para-methoxycinnamate | 5 | 5 | 5 | 5 | 5 | 5 | 5 | 5 |
| 5. copolymer of polyoxyethylene/methylpolysiloxane(*1) | 2 | 2 | 2 | 2 | 2 | 2 | 2 | 2 |
| 6. dextrin fatty acid ester | 2 | 2 | 2 | 2 | 2 | 2 | 2 | 2 |
| 7. 1,3-butylene glycol | 10 | 10 | 10 | 10 | 10 | 10 | 10 | 10 |
| 8. preservative | q.s. | q.s. | q.s. | q.s. | q.s. | q.s. | q.s. | q.s. |
| 9. refined water | bal | bal | bal | bal | bal | bal | bal | bal |
| 10. perfume | q.s. | q.s. | q.s. | q.s. | q.s. | q.s. | q.s. | q.s. |
| 11. titanium oxide dispersion (a-1)[Example 1] | 50 | — | — | — | — | — | — | — |
| 12. zinc oxide dispersion (a-2)[Example 2] | — | 35 | — | — | — | — | — | — |
| 13. zinc oxide dispersion (a-3)[Example 3] | — | — | 40 | — | — | — | — | — |
| 14. zinc oxide dispersion (a-4)[Example 4] | — | — | — | 40 | — | — | — | — |
| 15. titanium oxide dispersion (a-5)[Example 5] | — | — | — | — | 50 | — | — | — |
| 16. titanium oxide dispersion (a-6)[Example 6] | — | — | — | — | — | 50 | — | — |
| 17. zinc oxide dispersion (a-7)[Example 7] | — | — | — | — | — | — | 40 | — |
| 18. titanium oxide dispersion (a-9)[Comp. Example 1] | — | — | — | — | — | — | — | 40 |
| (evaluation items) | | | | | | | | |
| 1. Dispersion stability test | | | | | | | | |
| Cohesion of powder particles | ◉ | ◉ | ◉ | ◉ | ◉ | ◉ | ◉ | ○ |
| 2. Sensory evaluation | | | | | | | | |
| Dry feeling upon use | ◉ | ◉ | ◉ | ◉ | ◉ | ◉ | ◉ | ◉ |
| Spreadability | ◉ | ◉ | ◉ | ◉ | ◉ | ◉ | ◉ | ◉ |
| Transparency of cosmetic film | ◉ | ◉ | ◉ | ◉ | ◉ | ◉ | ◉ | △ |
| Lack of stickiness after application | ◉ | ◉ | ◉ | ◉ | ◉ | ◉ | ◉ | ◉ |
| Smoothness after application | ◉ | ◉ | ◉ | ◉ | ◉ | ◉ | ◉ | ◉ |
| Fresh feeling upon use | ◉ | ◉ | ◉ | ◉ | ◉ | ◉ | ◉ | ◉ |
| Sunscreening effect | ◉ | ◉ | ◉ | ◉ | ◉ | ◉ | ◉ | ◉ |

*1 Silicone KF6017 (product of Sinetsu Chemical Industries Co., Ltd.)
C.E.: Comparative Example
q.s.: quantum sufficit
bal: balance

TABLE 2

| | Example | | | | | | | | | | C.E. |
|---|---|---|---|---|---|---|---|---|---|---|---|
| component (%) | 56 | 57 | 58 | 59 | 60 | 61 | 62 | 63 | 64 | 65 | 4 |
| 1. triisooctanoic acid glyceryl | 5 | 5 | — | 5 | 5 | 5 | 5 | 5 | 5 | 5 | 5 |
| 2. dimethylpolysiloxane (6cSt) | 5 | 5 | 5 | 5 | 5 | 5 | 5 | 5 | 5 | 5 | 5 |
| 3. decamethylcyclopentasiloxane | — | 10 | 15 | 10 | 10 | 10 | — | 10 | 10 | — | — |

TABLE 2-continued

| component (%) | Example 56 | 57 | 58 | 59 | 60 | 61 | 62 | 63 | 64 | 65 | C.E. 4 |
|---|---|---|---|---|---|---|---|---|---|---|---|
| 4. 2-ethylhexyl para-methoxycinnamate | 5 | 5 | 5 | 5 | 5 | 5 | 5 | 5 | 5 | 5 | 5 |
| 5. copolymer of polyoxyethylene/methylpolysiloxane(*1) | 2 | 2 | 2 | 2 | 2 | 2 | 2 | 2 | 2 | 2 | 2 |
| 6. dextrin fatty acid ester | 2 | 2 | 2 | 2 | 2 | 2 | 2 | 2 | 2 | 2 | 2 |
| 7. 1,3-butylene glycol | 10 | 10 | 10 | 10 | 10 | 10 | 10 | 10 | 10 | 10 | 10 |
| 8. preservative | q.s. | q.s. | q.s. | q.s. | q.s. | q.s. | q.s. | q.s. | q.s. | q.s. | q.s. |
| 9. refined water | bal | bal | bal | bal | bal | bal | bal | bal | bal | bal | bal |
| 10. perfume | q.s. | q.s. | q.s. | q.s. | q.s. | q.s. | q.s. | q.s. | q.s. | q.s. | q.s. |
| 11. titanium oxide dispersion (b-1)[Example 9] | 50 | — | — | — | — | — | — | — | — | — | — |
| 12. zinc oxide dispersion (b-2)[Example 10] | — | 40 | — | — | — | — | — | — | — | — | — |
| 13. zinc oxide dispersion (b-3)[Example 11] | — | — | 40 | — | — | — | — | — | — | — | — |
| 14. titanium oxide dispersion (b-4)[Example 12] | — | — | — | 40 | — | — | — | — | — | — | — |
| 15. zinc oxide dispersion (b-5)[Example 13] | — | — | — | — | 40 | — | — | — | — | — | — |
| 16. zinc oxide dispersion (b-6)[Example 14] | — | — | — | — | — | 40 | — | — | — | — | — |
| 17. titanium oxide dispersion (b-7)[Example 15] | — | — | — | — | — | — | 50 | — | — | — | — |
| 18. zinc oxide dispersion (b-8)[Example 16] | — | — | — | — | — | — | — | 40 | — | — | — |
| 19. zinc oxide dispersion (b-9)[Example 17] | — | — | — | — | — | — | — | — | 40 | — | — |
| 20. titanium oxide dispersion (b-10)[Example 18] | — | — | — | — | — | — | — | — | — | 50 | — |
| 21. titanium oxide dispersion (b-12)[Comp. Example 2] | — | — | — | — | — | — | — | — | — | — | 50 |
| (evaluation items) | | | | | | | | | | | |
| 1. Dispersion stability test | | | | | | | | | | | |
| Cohesion of powder particles | ◉ | ◉ | ◉ | ◉ | ◉ | ◉ | ◉ | ◉ | ◉ | ◉ | ○ |
| 2. Sensory evaluation | | | | | | | | | | | |
| Dry feeling upon use | ◉ | ◉ | ◉ | ◉ | ◉ | ◉ | ◉ | ◉ | ◉ | ◉ | ◉ |
| Spreadability | ◉ | ◉ | ◉ | ◉ | ◉ | ◉ | ◉ | ◉ | ◉ | ◉ | ◉ |
| Transparency of cosmetic film | ◉ | ◉ | ◉ | ◉ | ◉ | ◉ | ◉ | ◉ | ◉ | ◉ | ◉ |
| Lack of stickness after application | ◉ | ◉ | ◉ | ◉ | ◉ | ◉ | ◉ | ◉ | ◉ | ◉ | △ |
| Smoothness after application | ◉ | ◉ | ◉ | ◉ | ◉ | ◉ | ◉ | ◉ | ◉ | ◉ | ◉ |
| Fresh feeling upon use | ◉ | ◉ | ◉ | ◉ | ◉ | ◉ | ◉ | ◉ | ◉ | ◉ | ◉ |
| Sunscreening effect | ◉ | ◉ | ◉ | ◉ | ◉ | ◉ | ◉ | ◉ | ◉ | ◉ | ◉ |

*1 Silicone KF6017 (product of Sinetsu Chemical Industries Co., Ltd.)
C.E.: Comparative Example
q.s.: quantum sufficit
bal: balance

TABLE 3

| component (%) | Example 67 | 68 | 69 | 70 | 71 | 72 | C.E. 3 |
|---|---|---|---|---|---|---|---|
| 1. triisooctanoic acid glyceryl | 5 | 5 | 5 | — | 5 | 5 | 5 |
| 2. dimethylpolysiloxane (6cSt) | 5 | 5 | 5 | 5 | 5 | 5 | 5 |
| 3. decamethylcyclopentasiloxane | — | — | 10 | 20 | — | — | 10 |
| 4. 2-ethylhexyl para-methoxycinnamate | 5 | 5 | 5 | 5 | 5 | 5 | 5 |
| 5. copolymer of polyoxyethylene/methylpolysiloxane(*1) | 2 | 2 | 2 | 2 | 2 | 2 | 2 |
| 6. dextrin fatty acid ester | 2 | 2 | 2 | 2 | 2 | 2 | 2 |
| 7. 1,3-butylene glycol | 10 | 10 | 10 | 10 | 10 | 10 | 10 |
| 8. preservative | q.s. | q.s. | q.s. | q.s. | q.s. | q.s. | q.s. |
| 9. refined water | bal | bal | bal | bal | bal | bal | bal |
| 10. perfume | q.s. | q.s. | q.s. | q.s. | q.s. | q.s. | q.s. |
| 11. titanium oxide dispersion (c-1)[Example 20] | 50 | — | — | — | — | — | — |
| 12. zinc oxide dispersion (c-2)[Example 21] | — | 50 | — | — | — | — | — |
| 13. zinc oxide dispersion (c-3)[Example 22] | — | — | 40 | — | — | — | — |
| 14. zinc oxide dispersion (c-4)[Example 23] | — | — | — | 35 | — | — | — |
| 15. zinc oxide dispersion (c-5)[Example 24] | — | — | — | — | 50 | — | — |
| 16. titanium oxide dispersion (c-6)[Example 25] | — | — | — | — | — | 50 | — |
| 17. titanium oxide dispersion (a-9)[Comp. Example 1] | — | — | — | — | — | — | 40 |
| (evaluation items) | | | | | | | |
| 1. Dispersion stability test | | | | | | | |
| Cohesion of powder particles | ◉ | ◉ | ◉ | ◉ | ◉ | ◉ | ○ |
| 2. Sensory evaluation | | | | | | | |
| Dry feeling upon use | ◉ | ◉ | ◉ | ◉ | ◉ | ◉ | ◉ |
| Spreadability | ◉ | ◉ | ◉ | ◉ | ◉ | ◉ | ◉ |
| Transparency of cosmetic film | ◉ | ◉ | ◉ | ◉ | ◉ | ◉ | △ |
| Lack of stickness after application | ◉ | ◉ | ◉ | ◉ | ◉ | ◉ | ◉ |

TABLE 3-continued

| component (%) | Example 67 | 68 | 69 | 70 | 71 | 72 | C.E. 3 |
|---|---|---|---|---|---|---|---|
| Smoothness after application | ◎ | ◎ | ◎ | ◎ | ◎ | ◎ | ◎ |
| Fresh feeling upon use | ◎ | ◎ | ◎ | ◎ | ◎ | ◎ | ◎ |
| Sunscreening effect | ◎ | ◎ | ◎ | ◎ | ◎ | ◎ | ◎ |

*1 Silicone KF6017 (product of Sinetsu Chemical Industries Co., Ltd.)
C.E.: Comparative Example
q.s.: quantum sufficit
bal: balance

TABLE 4

| component (%) | Example 74 | 75 | 76 | 77 | 78 | 79 | 80 | 81 | 82 | C.E. 4 |
|---|---|---|---|---|---|---|---|---|---|---|
| 1. triisooctanoic acid glyceryl | 5 | 5 | 5 | 5 | 5 | 5 | 5 | — | 5 | 5 |
| 2. dimethylpolysiloxane (6cSt) | 5 | 5 | 5 | 5 | 5 | 5 | 5 | 5 | 5 | 5 |
| 3. decamethylcyclopentasiloxane | — | 10 | 10 | — | 10 | — | 10 | 20 | — | — |
| 4. 2-ethylhexyl para-methoxycinnamate | 5 | 5 | 5 | 5 | 5 | 5 | 5 | 5 | 5 | 5 |
| 5. copolymer of polyoxyethylene/methylpolysiloxane(*1) | 2 | 2 | 2 | 2 | 2 | 2 | 2 | 2 | 2 | 2 |
| 6. dextrin fatty acid ester | 2 | 2 | 2 | 2 | 2 | 2 | 2 | 2 | 2 | 2 |
| 7. 1,3-butylene glycol | 10 | 10 | 10 | 10 | 10 | 10 | 10 | 10 | 10 | 10 |
| 8. preservative | q.s. | q.s. | q.s. | q.s. | q.s. | q.s. | q.s. | q.s. | q.s. | q.s. |
| 9. refined water | bal | bal | bal | bal | bal | bal | bal | bal | bal | bal |
| 10. perfume | q.s. | q.s. | q.s. | q.s. | q.s. | q.s. | q.s. | q.s. | q.s. | q.s. |
| 11. titanium oxide dispersion (d-1)[Example 27] | 50 | — | — | — | — | — | — | — | — | — |
| 12. zinc oxide dispersion (d-2)[Example 28] | — | 40 | — | — | — | — | — | — | — | — |
| 13. zinc oxide dispersion (d-3)[Example 29] | — | — | 40 | — | — | — | — | — | — | — |
| 14. titanium oxide dispersion (d-4)[Example 30] | — | — | — | 50 | — | — | — | — | — | — |
| 15. titanium oxide dispersion (d-5)[Example 31] | — | — | — | — | 40 | — | — | — | — | — |
| 16. zinc oxide dispersion (d-6)[Example 32] | — | — | — | — | — | 50 | — | — | — | — |
| 17. titanium oxide dispersion (d-7)[Example 33] | — | — | — | — | — | — | 40 | — | — | — |
| 18. zinc oxide dispersion (d-8)[Example 34] | — | — | — | — | — | — | — | 35 | — | — |
| 19. titanium oxide dispersion (d-9)[Example 35] | — | — | — | — | — | — | — | — | 50 | — |
| 20. titanium oxide dispersion (b-12)[Comp. Example 2] | — | — | — | — | — | — | — | — | — | 50 |
| (evaluation items) | | | | | | | | | | |
| 1. Dispersion stability test | | | | | | | | | | |
| Cohesion of powder particles | ◎ | ◎ | ◎ | ◎ | ◎ | ◎ | ◎ | ◎ | ◎ | ○ |
| 2. Sensory evaluation | | | | | | | | | | |
| Dry feeling upon use | ◎ | ◎ | ◎ | ◎ | ◎ | ◎ | ◎ | ◎ | ◎ | ◎ |
| Spreadability | ◎ | ◎ | ◎ | ◎ | ◎ | ◎ | ◎ | ◎ | ◎ | ◎ |
| Transparency of cosmetic film | ◎ | ◎ | ◎ | ◎ | ◎ | ◎ | ◎ | ◎ | ◎ | Δ |
| Lack of stickiness after application | ◎ | ◎ | ◎ | ◎ | ◎ | ◎ | ◎ | ◎ | ◎ | ◎ |
| Smoothness after application | ◎ | ◎ | ◎ | ◎ | ◎ | ◎ | ◎ | ◎ | ◎ | ◎ |
| Fresh feeling upon use | ◎ | ◎ | ◎ | ◎ | ◎ | ◎ | ◎ | ◎ | ◎ | ◎ |
| Sunscreening effect | ◎ | ◎ | ◎ | ◎ | ◎ | ◎ | ◎ | ◎ | ◎ | ◎ |

*1 Silicone KF6017 (product of Sinetsu Chemical Industries Co., Ltd.)
C.E.: Comparative Example
q.s.: quantum sufficit
bal: balance

TABLE 5

| component (%) | Example 84 | 85 | 86 | 87 | 88 | 89 | 90 | 91 | 92 | 93 | C.E. 4 |
|---|---|---|---|---|---|---|---|---|---|---|---|
| 1. triisooctanoic acid glyceryl | 5 | 5 | — | 5 | 5 | 5 | 5 | 5 | 5 | 5 | 5 |
| 2. dimethylpolysiloxane (6cSt) | 5 | 5 | 5 | 5 | 5 | 5 | 5 | 5 | 5 | 5 | 5 |
| 3. decamethylcyclopentasiloxane | — | 10 | 15 | 10 | 10 | 10 | — | 10 | 10 | — | — |
| 4. 2-ethylhexyl para-methoxycinnamate | 5 | 5 | 5 | 5 | 5 | 5 | 5 | 5 | 5 | 5 | 5 |
| 5. copolymer of polyoxyethylene/methylpolysiloxane(*1) | 2 | 2 | 2 | 2 | 2 | 2 | 2 | 2 | 2 | 2 | 2 |
| 6. dextrin fatty acid ester | 2 | 2 | 2 | 2 | 2 | 2 | 2 | 2 | 2 | 2 | 2 |
| 7. 1,3-butylene glycol | 10 | 10 | 10 | 10 | 10 | 10 | 10 | 10 | 10 | 10 | 10 |
| 8. preservative | q.s. | q.s. | q.s. | q.s. | q.s. | q.s. | q.s. | q.s. | q.s. | q.s. | q.s. |
| 9. refined water | bal | bal | bal | bal | bal | bal | bal | bal | bal | bal | bal |
| 10. perfume | q.s. | q.s. | q.s. | q.s. | q.s. | q.s. | q.s. | q.s. | q.s. | q.s. | q.s. |
| 11. titanium oxide dispersion (e-1)[Example 37] | 50 | — | — | — | — | — | — | — | — | — | — |
| 12. zinc oxide dispersion (e-2)[Example 38] | — | 40 | — | — | — | — | — | — | — | — | — |
| 13. zinc oxide dispersion (e-3)[Example 39] | — | — | 40 | — | — | — | — | — | — | — | — |

TABLE 5-continued

| component (%) | Example | | | | | | | | | | C.E. |
|---|---|---|---|---|---|---|---|---|---|---|---|
| | 84 | 85 | 86 | 87 | 88 | 89 | 90 | 91 | 92 | 93 | 4 |
| 14. titanium oxide dispersion (e-4)[Example 40] | — | — | — | 40 | — | — | — | — | — | — | — |
| 15. zinc oxide dispersion (e-5)[Example 41] | — | — | — | — | 40 | — | — | — | — | — | — |
| 16. zinc oxide dispersion (e-6)[Example 42] | — | — | — | — | — | 40 | — | — | — | — | — |
| 17. zinc oxide dispersion (e-7)[Example 43] | — | — | — | — | — | — | 50 | — | — | — | — |
| 18. zinc oxide dispersion (e-8)[Example 44] | — | — | — | — | — | — | — | 40 | — | — | — |
| 19. zinc oxide dispersion (e-9)[Example 45] | — | — | — | — | — | — | — | — | 40 | — | — |
| 20. titanium oxide dispersion (e-10)[Example 46] | — | — | — | — | — | — | — | — | — | 50 | — |
| 21. titanium oxide dispersion (b-12)[Comp. Example 2] | — | — | — | — | — | — | — | — | — | — | 50 |
| (evaluation items) | | | | | | | | | | | |
| 1. Dispersion stability test | | | | | | | | | | | |
| Cohesion of powder particles | ⊚ | ⊚ | ⊚ | ⊚ | ⊚ | ⊚ | ⊚ | ⊚ | ⊚ | ⊚ | ○ |
| 2. Sensory evaluation | | | | | | | | | | | |
| Dry feeling upon use | ⊚ | ⊚ | ⊚ | ⊚ | ⊚ | ⊚ | ⊚ | ⊚ | ⊚ | ⊚ | ⊚ |
| Spreadability | ⊚ | ⊚ | ⊚ | ⊚ | ⊚ | ⊚ | ⊚ | ⊚ | ⊚ | ⊚ | ⊚ |
| Transparency of cosmetic film | ⊚ | ⊚ | ⊚ | ⊚ | ⊚ | ⊚ | ⊚ | ⊚ | ⊚ | ⊚ | ⊚ |
| Lack of stickness after application | ⊚ | ⊚ | ⊚ | ⊚ | ⊚ | ⊚ | ⊚ | ⊚ | ⊚ | ⊚ | Δ |
| Smoothness after application | ⊚ | ⊚ | ⊚ | ⊚ | ⊚ | ⊚ | ⊚ | ⊚ | ⊚ | ⊚ | ⊚ |
| Fresh feeling upon use | ⊚ | ⊚ | ⊚ | ⊚ | ⊚ | ⊚ | ⊚ | ⊚ | ⊚ | ⊚ | ⊚ |
| Sunscreening effect | ⊚ | ⊚ | ⊚ | ⊚ | ⊚ | ⊚ | ⊚ | ⊚ | ⊚ | ⊚ | ⊚ |

*1 Silicone KF6017 (product of Sinetsu Chemical Industries Co., Ltd.)
C.E.: Comparative Example
q.s.: quantum sufficit
bal: balance

TABLE 6

| component (%) | Example | | | | | C.E. | |
|---|---|---|---|---|---|---|---|
| | 55 | 66 | 73 | 83 | 94 | 5 | 6 |
| 1. triisooctanoic acid glyceryl | 5 | 5 | 5 | 5 | 5 | 5 | 5 |
| 2. dimethylpolysiloxane (6cSt) | 5 | 5 | 5 | 5 | 5 | 5 | 5 |
| 3. decamethylcyclopentasiloxane | 30 | 30 | 30 | 30 | 30 | 30 | 30 |
| 4. 2-ethylhexyl para-methoxycinnamate | 5 | 5 | 5 | 5 | 5 | 5 | 5 |
| 5. copolymer of polyoxyethylene/methylpolysiloxane(*1) | 2 | 2 | 2 | 2 | 2 | 2 | 2 |
| 6. dextrin fatty acid ester | 2 | 2 | 2 | 2 | 2 | 2 | 2 |
| 7. 1,3-butylene glycol | 10 | 10 | 10 | 10 | 10 | 10 | 10 |
| 8. preservative | q.s. | q.s. | q.s. | q.s. | q.s. | q.s. | q.s. |
| 9. refined water | bal | bal | bal | bal | bal | bal | bal |
| 10. perfume | q.s. | q.s. | q.s. | q.s. | q.s. | q.s. | q.s. |
| 11. titanium oxide composition (a-8)[Example 8] | 20 | — | — | — | — | — | — |
| 12. titanium oxide composition (b-11)[Example 19] | — | 20 | — | — | — | — | — |
| 13. titanium oxide composition (c-7)[Example 26] | — | — | 20 | — | — | — | — |
| 14. titanium oxide composition (d-10)[Example 36] | — | — | — | 20 | — | — | — |
| 15. titanium oxide composition (e-11)[Example 47] | — | — | — | — | 20 | — | — |
| 16. titanium oxide | — | — | — | — | — | 20 | — |
| 17. silicone treated titanium oxide | — | — | — | — | — | — | 20 |
| (evaluation items) | | | | | | | |
| 1. Dispersion stability test | | | | | | | |
| Cohesion of powder particles | ⊚ | ⊚ | ⊚ | ⊚ | ⊚ | X | X |
| 2. Sensory evaluation | | | | | | | |
| Dry feeling upon use | ⊚ | ⊚ | ⊚ | ⊚ | ⊚ | X | Δ |
| Spreadability | ⊚ | ⊚ | ⊚ | ⊚ | ⊚ | X | Δ |
| Transparency of cosmetic film | ⊚ | ⊚ | ⊚ | ⊚ | ⊚ | X | X |
| Lack of stickness after application | ⊚ | ⊚ | ⊚ | ⊚ | ⊚ | Δ | Δ |
| Smoothness after application | ⊚ | ⊚ | ⊚ | ⊚ | ⊚ | X | X |
| Fresh feeling upon use | ⊚ | ⊚ | ⊚ | ⊚ | ⊚ | Δ | Δ |
| Sunscreening effect | ⊚ | ⊚ | ⊚ | ⊚ | ⊚ | X | X |

*1 Silicone KF6017 (product of Sinetsu Chemical Industries Co., Ltd.)
C.E.: Comparative Example
q.s.: quantum sufficit
bal: balance

What is claimed is:

1. A powder dispersion in oil composition comprising powder, oil and a copolymer wherein
said powder is dispersed in said oil, which oil contains said copolymer composed of constituent units from a monomer (A) and constituent units from a monomer (B), wherein
said monomer (A) is an organopolysiloxane monomer possessing a radical polymerization group possible to polymerize with monomer (B) and is represented by the formula (I), $$W(X)_a(Si)(Y)_b(Z)_c \tag{I}$$

wherein
W represents a vinyl group which can contain a substitution group,
X represents a divalent bonding group,
Y represents a hydrogen atom, an alkyl group of 1 to 10 carbon atoms, an aryl group or an alkoxy group,
Z represents a monovalent siloxane polymer,
a is an integer of 0 to 1,
b is an integer of 0 to 2,
c is an integer of 1 to 3, and
b+c=3, and
said monomer (B) consists essentially of one more monomers selected from the group consisting of a vinyl monomer containing a nitrogen group, a vinyl monomer containing a polyoxyalkylene group, a vinyl monomer containing a polylactone group, a vinyl monomer containing an alcohol hydroxyl group and a vinyl monomer containing an anionic group.

2. The powder dispersion in oil composition of claim 1, wherein the content of said constituent units from a monomer (A) in said copolymer is larger than 10% by weight.

3. The powder dispersion in oil composition of claim 1, wherein the amount of copolymer to powder is larger than 1% by weight.

4. The powder dispersion in oil composition of claim 1, wherein said vinyl monomer (B) containing a nitrogen group is one or more vinyl monomers selected from the group consisting of acrylamide, methacrylamide, N-vinylpyrrolidone and N-vinylacetamide.

5. The powder dispersion in oil composition of claim 1, wherein said vinyl monomer (B) containing a polyoxyalkylene group is represented by the formula (II), $$J(K)_p(Q)_sT \tag{II}$$

wherein
J represents a vinyl group which can contain a substitution group,
K represents a divalent bonding group,
Q represents a polyoxyalkylene group represented by —$(CH_2)_tO$— and
T represents a hydrogen atom, an alkyl group of 1 to 10 carbon atoms, or an organic group represented by $R^1$—(CO)—, wherein
p is an integer of 0 or 1,
s is an integer larger than 1,
t is an integer of 1 to 50, and
$R^1$ represents an alkyl group of 1 to 5 carbon atoms.

6. The powder dispersion in oil composition of claim 5, wherein in said formula (2) vinyl monomer (B) containing a polyoxyalkylene t is an integer larger than 3.

7. The powder dispersion in oil composition of claim 5, wherein t of the formula (2) vinyl monomer (B) containing a polyoxyalkylene is 3.

8. The powder dispersion in oil composition of claim 1, wherein said vinyl monomer (B) containing a polylactone group is represented by the formula (III), $$J(K)_p(L)_qM \tag{III}$$

wherein
J represents a vinyl group which can contain a substitution group,
K represents a divalent bonding group,
L represents a lactone group represented by —C(=O)$(CR_2)_r$CHRO—, and
M represents a hydrogen atom, an acetyl group, wherein
p is an integer of 0 or 1,
q is an integer larger than 1,
r is an integer of 4 to 6,
R represents a hydrogen atom or an alkyl group of 1 to 12 carbon atoms.

9. The powder dispersion in oil composition of claim 1, wherein said vinyl monomer (B) containing an alcohol hydroxyl group is represented by the formula (IV), $$J(K)_sU \tag{IV}$$

wherein
J represents a vinyl group which can contain a substitution group,
K represents a divalent bonding group,
U represents an organic group containing an alcohol hydroxyl group, wherein
s is an integer of 0 or 1.

10. The powder dispersion in oil composition of claim 1, wherein said vinyl monomer (B) containing an anionic group is selected from the group consisting of a vinyl monomer containing carboxylic acid group, a vinyl monomer containing a phosphorus acid group, a vinyl monomer containing a sulfonic acid group.

11. A cosmetic composition comprising components (1) and (2), wherein
(1) is 0.01 to 98% by weight of the powder dispersion in oil composition comprising powder, oil and a copolymer, wherein said powder is dispersed in said oil which oil contains said copolymer composed of constituent units from a monomer (A) and constituent units from a monomer (B),
(2) is balance of at least one cosmetic component; wherein
said monomer (A) is an organopolysiloxane monomer represented by the formula (I), $$W(X)_aSi(Y)_b(Z)_c \tag{I}$$

wherein
W represents a vinyl group which can contain a substitution group,
X represents a divalent bonding group,
Y represents a hydrogen atom, an alkyl group of 1 to 10 carbon atoms, an aryl group or an alkoxy group,
Z represents a monovalent siloxane polymer,
a is an integer of 0 or 1,
b is an integer of 0 to 2,
c is an integer of 1 to 3, and
b+c=3, and
said monomer (B) consists essentially of one or more monomers selected from the group consisting of a vinyl monomer containing a nitrogen group, a vinyl monomer containing a polyoxyalkylene group, a vinyl monomer containing a polylactone group, a vinyl monomer containing an alcohol hydroxyl group and a vinyl monomer containing an anionic group.

12. The cosmetic composition of claim 11, wherein said vinyl monomer (B) containing a nitrogen group is one or more vinyl monomers selected from the group consisting of acrylamide, methacrylamide, N-vinylpyrrolidone and N-vinylacetamide.

13. The cosmetic composition of claim 11, wherein said vinyl monomer (B) containing a polyoxyalkylene group is represented by the formula (II), $$J(K)_p(Q)_sT \qquad (II)$$

wherein

J represents a vinyl group which can contain a substitution group,

K represents a divalent bonding group,

Q represents a polyoxyalkylene group represented by —(CH$_2$)$_t$O—, and

T represents a hydrogen atom, an alkyl group of 1 to 10 carbon atoms, or an organic group represented by R$^1$—(CO)—, wherein p is an integer of 0 or 1, s is an integer larger than 1, t is an integer of 1 to 50, and R$^1$ represents an alkyl group of 1 to 5 carbon atoms.

14. The cosmetic composition of claim 13, wherein said formula (2) vinyl monomer (B) containing a polyoxyalkylene t is an integer larger than 3.

15. The cosmetic composition of claim 13, wherein t of the formula (2) vinyl monomer (B) containing a polyoxyalkylene is 3.

16. The cosmetic composition of claim 11, wherein said vinyl monomer (B) containing a polylactone group is represented by the formula (III), $$J(K)_p(L)_qM \qquad (III)$$

wherein

J represents a vinyl group which can contain a substitution group,

K represents a divalent bonding group,

L represents a lactone group represented by —C(=O)(CR$_2$)$_r$CHRO— and

M represents a hydrogen atom, an acetyl group, wherein p is an integer of 0 or 1, q is an integer larger than 1, r is an integer of 4 to 6, R represents a hydrogen atom or an alkyl group of 1 to 12 carbon atoms.

17. The cosmetic composition of claim 11, wherein said vinyl monomer containing an alcohol hydroxyl group is represented by the formula (IV), $$J(K)_sU \qquad (IV)$$

wherein

J represents a vinyl group which can contain a substitution group,

K represents a divalent bonding group,

U represents an organic group containing an alcohol hydroxyl group, wherein s is an integer of 0 or 1.

18. The cosmetic composition of claim 11, wherein said vinyl monomer containing an anionic group is selected from the group consisting of a vinyl monomer containing carboxylic acid group, a vinyl monomer containing a phosphoric acid group, a vinyl monomer containing a sulfonic acid group.

19. The powder dispersion in oil composition of claim 1 wherein the monomer (A) is in an amount of 63 to 99% by weight and the monomer (B) is in an amount of 1 to 37% by weight based on the weight of monomer (A) and (B).

20. The cosmetic composition of claim 11, wherein the monomer (A) is in an amount of 63 to 99% by weight and the monomer (B) is in amount of 1 to 37% by weight based on the weight of monomer (A) and (B).

21. A powder dispersion in oil composition comprising powder, oil and a copolymer wherein said powder is dispersed in said oil and said copolymer is composed of constituent units from a monomer (A) and constituent units from a monomer (B), wherein said monomer (A) is an organopolysiloxane monomer represented by the formula (I), $$W(X)_aSi(Y)_b(Z)_c \qquad (I)$$

wherein

W represents a vinyl group which can contain a substitution group,

X represents a divalent bonding group,

Y represents a hydrogen atom, an alkyl group of 1 to 10 carbon atoms, an aryl group or an alkoxy group, Z represents a monovalent siloxane polymer, a is an integer of 0 or 1, b is an integer of 0 or 2, c is an integer of 1 to 3, and b+c=3, and said monomer (B) is one or more monomers selected from the group consisting of a vinyl monomer containing a polyoxyalkylene group, a vinyl monomer containing a polylactone group, a vinyl monomer containing a phosphoric acid group, a vinyl monomer containing a sulfonic acid group, acrylamide, methacrylamide, N-vinylpyrrolidone and N-vinylacetamide.

22. The powder dispersion in oil composition of claim 21, wherein said vinyl monomer (B) is a member selected from the group consisting of acrylamide, methacrylamide, N-vinylpyrrolidone and N-vinylacetamide.

23. The powder dispersion in oil composition of claim 21, wherein said vinyl monomer containing a polyoxyalkylene group is represented by the formula (II), $$J(K)_p(Q)_sT \qquad (II)$$

wherein

J represents a vinyl group which can contain a substitution group,

K represents a divalent bonding group,

Q represents a polyoxyalkylene group represented by —(CH$_2$)$_t$O— and

T represents a hydrogen atom, an alkyl group of 1 to 10 carbon atoms, or an organic group represented by R$^1$—(CO)—, wherein p is an integer of 0 or 1, s is an integer larger than 1, t is an integer of 1 to 50, and R$^1$ represents an alkyl group of 1 to 5 carbon atoms.

24. The powder dispersion in oil composition of claim 21, wherein said vinyl monomer containing a polylactone group is represented by the formula (III), $$J(K)_p(L)_qM \qquad (III)$$

wherein

J represents a vinyl group which can contain a substitution group,

K represents a divalent bonding group,

L represents a lactone group represented by —C(=O)(CR$_2$)$_r$CHRO—, and

M represents a hydrogen atom, an acetyl group, wherein p is an integer of 0 or 1, q is an integer larger than 1, r is an integer of 4 to 6, R represents a hydrogen atom or an alkyl group of 1 to 12 carbon atoms.

25. A cosmetic composition comprising components (1) and (2), wherein (1) is 0.01 to 98% by weight of the powder dispersion in oil composition comprising powder, oil and a copolymer, wherein said powder is dispersed in said oil and said copolymer is composed of constituent units from a monomer (A) and constituent units from a monomer (B), (2) is balance of at least one cosmetic component; wherein said monomer (A) is an organopolysiloxane monomer represented by the formula (I), $$W(X)_aSi(Y)_b(Z)_c \qquad (I)$$

wherein

W represents a vinyl group which can contain a substitution group,

X represents a divalent bonding group,

Y represents a hydrogen atom, an alkyl group of 1 to 10 carbon atoms, an aryl group or an alkoxy group, Z represents a monovalent siloxane polymer, a is an integer of 0 or 1, b is an integer of 0 to 2, c is an integer of 1 to 3, and b+c=3, and said monomer (B) is one or more monomers selected from the group consisting of a vinyl monomer containing a polyoxyalkylene group, a vinyl monomer containing a polylactone group, a vinyl monomer containing a phosphoric acid group, a vinyl monomer containing a sulfonic acid group, acrylamide, methacrylamide, N-vinylpyrrolidone and N-vinylacetamide.

26. The cosmetic composition of claim 25, wherein said vinyl monomer (B) is a member selected from the group consisting of acrylamide, methacrylamide, N-vinylpyrrolidone and N-vinylacetamide.

27. The cosmetic composition of claim 25, wherein said vinyl monomer containing a polyoxyalkylene group is represented by the formula (II), $$J(K)_p(Q)_sT \qquad (II)$$

wherein

J represents a vinyl group which can contain a substitution group,

K represents a divalent bonding group,

Q represents a polyoxyalkylene group represented by —(CH$_2$)$_t$O— and

T represents a hydrogen atom, an alkyl group of 1 to 10 carbon atoms, or an organic group represented by R$^1$—(CO)—, wherein p is an integer of 0 or 1, s is an integer larger than 1, t is an integer of 1 to 50, and R$^1$ represents an alkyl group of 1 to 5 carbon atoms.

28. The cosmetic composition of claim 27, wherein said formula (2) vinyl monomer containing a polyoxyalkylene t is an integer larger than 3.

29. The cosmetic composition of claim 25, wherein said vinyl monomer containing a polylactone group is represented by the formula (III), $$J(K)_p(L)_qM \qquad (III)$$

wherein

J represents a vinyl group which can contain a substitution group,

K represents a divalent bonding group,

L represents a lactone group represented by —C(=O)(CR$_2$)$_r$CHRO—, and

M represents a hydrogen atom, an acetyl group, wherein p is an integer or 0 or 1, q is an integer larger than 1, r is an integer of 4 to 6, R represents a hydrogen atom or an alkyl group of 1 to 12 carbon atoms.

30. The powder dispersion in oil composition of claim 21 wherein the monomer (A) is in an amount of 63 to 99% by weight and the monomer (B) is in an amount of 1 to 37% by weight based on the weight of monomer (A) and (B).

31. The cosmetic composition of claim 25, wherein the monomer (A) is in an amount of 63 to 99% by weight and the monomer (B) is in an amount of 1 to 37% by weight based on the weight of monomer (A) and (B).

* * * * *

UNITED STATES PATENT AND TRADEMARK OFFICE
CERTIFICATE OF CORRECTION

PATENT NO. : 6,342,239 B1
DATED : January 29, 2002
INVENTOR(S) : Kiyomi Tachibana et al.

It is certified that error appears in the above-identified patent and that said Letters Patent is hereby corrected as shown below:

<u>Title page,</u>
Item [73], change "[73] Assignee: Kose Corporation, Tokyo (JP)" to
-- [73] Assignees: Kose Corporation and Shin-Etsu Chemical Co., Ltd., both of Tokyo (JP) --

Signed and Sealed this

Thirteenth Day of April, 2004

JON W. DUDAS
*Acting Director of the United States Patent and Trademark Office*